US008226293B2

(12) United States Patent
Faries, Jr. et al.

(10) Patent No.: US 8,226,293 B2
(45) Date of Patent: Jul. 24, 2012

(54) METHOD AND APPARATUS FOR MEASUREMENT AND CONTROL OF TEMPERATURE FOR INFUSED LIQUIDS

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 11/677,673

(22) Filed: Feb. 22, 2007

(65) Prior Publication Data

US 2008/0205481 A1   Aug. 28, 2008

(51) Int. Cl.
*G01K 13/00* (2006.01)
*G01K 1/00* (2006.01)
(52) U.S. Cl. .................... 374/138; 374/208; 374/135
(58) Field of Classification Search .................. 374/135, 374/138, 208
See application file for complete search history.

(56) References Cited

U.S. PATENT DOCUMENTS

| 522,866 A | 7/1894 | Weinhagen et al. |
| 558,976 A | 4/1896 | Noble |
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |

(Continued)

FOREIGN PATENT DOCUMENTS

DE   3709122 A1   9/1988

(Continued)

OTHER PUBLICATIONS

Health Devices, vol. 25, No. 10, Oct. 1996.

(Continued)

*Primary Examiner* — Lisa Caputo
*Assistant Examiner* — Mirellys Jagan
(74) *Attorney, Agent, or Firm* — Edell, Shapiro & Finnan, LLC

(57) ABSTRACT

A device according to present invention embodiments measures the temperature of fluid within an IV line at selected locations. The device may be in the form of a fitting including a projection in fluid communication with a fluid channel to receive a temperature sensor. A thermally conductive receptacle may be disposed in the projection to receive the temperature sensor and partially extends into the fluid channel for contact with the fluid. The temperature sensor may be coupled to a temperature display device and/or controller to display the measured temperature and/or control a thermal element to regulate fluid temperature. The fitting may further include a looped configuration and/or a control valve that controls the flow of fluid through the fluid channel. In addition, the device may further be connected to, or be in the form of, a needle hub to measure fluid temperature proximate the entry site on a patient.

25 Claims, 16 Drawing Sheets

U.S. PATENT DOCUMENTS

| | | | |
|---|---|---|---|
| 1,847,573 A | 3/1932 | Rupp | |
| 1,847,954 A | 3/1932 | Fisher | |
| 1,960,417 A | 5/1934 | Pain, Jr. | |
| 1,982,213 A | 11/1934 | Hopkins | |
| 1,987,119 A | 1/1935 | Long | |
| 1,995,302 A | 3/1935 | Goldstein | |
| 2,063,902 A | 12/1936 | Beasley | |
| 2,087,586 A | 7/1937 | Tishman | |
| 2,124,293 A | 7/1938 | Goldstein | |
| 2,204,764 A | 6/1940 | Mayo | |
| 2,254,994 A | 9/1941 | Butland | |
| 2,470,481 A | 5/1949 | Freeman | |
| 2,701,789 A | 2/1955 | White | |
| 2,766,907 A | 10/1956 | Wallace, Jr. | |
| 2,880,764 A | 4/1959 | Pelavin | |
| 2,910,981 A | 11/1959 | Wilson et al. | |
| 2,990,875 A | 7/1961 | Samuels et al. | |
| 3,140,716 A | 7/1964 | Harrison et al. | |
| 3,157,727 A | 11/1964 | Hardy et al. | |
| 3,247,851 A | 4/1966 | Seibert | |
| 3,293,868 A | 12/1966 | Gonzalez | |
| 3,370,153 A | 2/1968 | Du Fresne et al. | |
| 3,475,590 A | 10/1969 | Pins | |
| 3,485,245 A | 12/1969 | Lahr et al. | |
| 3,500,366 A | 3/1970 | Chesney et al. | |
| 3,526,134 A | 9/1970 | Schaus | |
| 3,551,641 A | 12/1970 | Truhan | |
| 3,563,090 A | 2/1971 | Deltour | |
| 3,590,215 A | 6/1971 | Anderson et al. | |
| 3,591,290 A | 7/1971 | Zinner et al. | |
| 3,596,515 A | 8/1971 | Cramer | |
| 3,612,059 A | 10/1971 | Ersek | |
| 3,614,385 A | 10/1971 | Horstmann | |
| 3,629,552 A | 12/1971 | Edging | |
| 3,636,767 A | 1/1972 | Duffy | |
| 3,640,277 A | 2/1972 | Adelberg | |
| 3,651,695 A | 3/1972 | Brown | |
| 3,845,661 A | 11/1974 | Hollweck et al. | |
| 3,895,741 A | 7/1975 | Nugent | |
| 3,908,652 A | 9/1975 | Weissinger | |
| 3,940,792 A | 2/1976 | Herleth | |
| 4,009,615 A | 3/1977 | Ruhl | |
| 4,038,519 A | 7/1977 | Foucras | |
| 4,063,551 A | 12/1977 | Sweeney | |
| 4,090,514 A | 5/1978 | Hinck et al. | |
| 4,098,123 A | 7/1978 | Granzow, Jr. | |
| 4,121,574 A | 10/1978 | Lester | |
| 4,138,890 A | 2/1979 | Brown | |
| 4,167,663 A | 9/1979 | Granzow, Jr. et al. | |
| 4,187,847 A | 2/1980 | Loeser | |
| 4,293,762 A | 10/1981 | Ogawa | |
| 4,309,592 A | 1/1982 | Le Boeuf | |
| 4,314,484 A | 2/1982 | Bowman | |
| 4,329,569 A | 5/1982 | Hjortsberg et al. | |
| 4,336,435 A | 6/1982 | Kashyap et al. | |
| 4,356,383 A | 10/1982 | Dahlberg | |
| 4,375,813 A | 3/1983 | Hessel | |
| 4,384,578 A | 5/1983 | Winkler | |
| 4,397,648 A | 8/1983 | Knute | |
| 4,430,077 A | 2/1984 | Mittleman et al. | |
| 4,430,078 A | 2/1984 | Sprague | |
| 4,432,761 A | 2/1984 | Dawe | |
| 4,464,563 A | 8/1984 | Jewett | |
| 4,476,877 A | 10/1984 | Barker | |
| 4,490,884 A | 1/1985 | Vickers | |
| 4,495,402 A | 1/1985 | Burdick et al. | |
| 4,498,901 A | 2/1985 | Finch | |
| 4,509,943 A | 4/1985 | Hanzawa | |
| 4,522,308 A | 6/1985 | Sullivan | |
| 4,523,078 A | 6/1985 | Lehmann | |
| 4,529,309 A | 7/1985 | Pettersson et al. | |
| 4,531,941 A | 7/1985 | Zasuwa | |
| 4,532,414 A | 7/1985 | Shah et al. | |
| 4,533,350 A | 8/1985 | Danby et al. | |
| 4,543,095 A | 9/1985 | Jensen | |
| 4,551,136 A | 11/1985 | Mandl | |
| 4,552,277 A | 11/1985 | Richardson et al. | |
| 4,572,536 A | 2/1986 | Doughty | |
| 4,585,441 A | 4/1986 | Archibald | |
| 4,586,691 A | 5/1986 | Kozlow | |
| 4,613,327 A | 9/1986 | Tegrarian et al. | |
| 4,614,514 A | 9/1986 | Carr et al. | |
| 4,625,086 A | 11/1986 | Karino | |
| 4,626,243 A | 12/1986 | Singh et al. | |
| 4,628,186 A | 12/1986 | Bergemann et al. | |
| 4,634,432 A | 1/1987 | Kocak | |
| 4,647,756 A | 3/1987 | Willis | |
| 4,651,813 A | 3/1987 | Witt et al. | |
| 4,657,004 A | 4/1987 | Coffey | |
| 4,673,820 A | 6/1987 | Kamen | |
| 4,674,977 A | 6/1987 | Hoselton | |
| 4,678,460 A | 7/1987 | Rosner | |
| 4,680,445 A | 7/1987 | Ogawa | |
| 4,680,977 A | 7/1987 | Conero et al. | |
| 4,682,979 A | 7/1987 | Girouard | |
| 4,684,367 A | 8/1987 | Schaffer et al. | |
| 4,705,505 A | 11/1987 | Fried | |
| 4,707,587 A | 11/1987 | Greenblatt | |
| 4,709,135 A | 11/1987 | Dietrich et al. | |
| 4,718,896 A | 1/1988 | Arndt et al. | |
| 4,735,609 A | 4/1988 | Comeau et al. | |
| 4,745,248 A | 5/1988 | Hayes | |
| 4,747,450 A | 5/1988 | Ikegame et al. | |
| 4,747,826 A | 5/1988 | Sassano | |
| 4,756,299 A | 7/1988 | Podella | |
| 4,759,749 A | 7/1988 | Verkaart | |
| 4,772,778 A | 9/1988 | Ogawa | |
| 4,781,548 A | 11/1988 | Alderson et al. | |
| 4,782,212 A | 11/1988 | Bakke | |
| 4,801,777 A | 1/1989 | Auerbach | |
| 4,804,367 A | 2/1989 | Smith et al. | |
| 4,808,159 A | 2/1989 | Wilson | |
| 4,823,833 A | 4/1989 | Hogan et al. | |
| 4,832,689 A | 5/1989 | Mauerer et al. | |
| 4,844,074 A | 7/1989 | Kurucz | |
| 4,844,397 A | 7/1989 | Skakoon et al. | |
| 4,847,470 A | 7/1989 | Bakke | |
| 4,859,360 A | 8/1989 | Suzuki et al. | |
| 4,874,033 A | 10/1989 | Chatelain et al. | |
| 4,874,359 A | 10/1989 | White et al. | |
| 4,878,537 A | 11/1989 | Verkaart | |
| 4,883,117 A | 11/1989 | Dobbs et al. | |
| 4,900,308 A | 2/1990 | Verkaart | |
| 4,904,848 A | 2/1990 | Colevas | |
| 4,906,816 A | 3/1990 | van Leerdam | |
| 4,934,152 A | 6/1990 | Templeton | |
| 4,934,336 A | 6/1990 | White | |
| 4,936,828 A | 6/1990 | Chiang | |
| 4,991,976 A * | 2/1991 | Byles | 374/135 |
| 4,994,021 A | 2/1991 | Smith et al. | |
| 5,013,889 A | 5/1991 | Bakke | |
| 5,019,047 A | 5/1991 | Kriesel | |
| 5,040,380 A * | 8/1991 | Gregory | 62/225 |
| 5,042,455 A | 8/1991 | Yue et al. | |
| 5,059,182 A | 10/1991 | Laing | |
| 5,061,241 A | 10/1991 | Stephens, Jr. et al. | |
| 5,061,630 A | 10/1991 | Knoopf et al. | |
| 5,063,994 A | 11/1991 | Verkaart | |
| 5,073,167 A | 12/1991 | Carr et al. | |
| 5,074,658 A | 12/1991 | Tavlarides et al. | |
| 5,075,167 A | 12/1991 | Yamauchi et al. | |
| 5,081,697 A | 1/1992 | Manella | |
| 5,096,078 A | 3/1992 | McQueeny | |
| 5,096,822 A | 3/1992 | Rosenkrans, Jr. et al. | |
| 5,097,898 A | 3/1992 | Verkaart | |
| 5,103,817 A | 4/1992 | Reisdorf et al. | |
| 5,106,373 A | 4/1992 | Augustine et al. | |
| 5,108,372 A | 4/1992 | Swenson | |
| 5,125,069 A | 6/1992 | O'Boyle | |
| 5,125,900 A | 6/1992 | Teves | |
| 5,129,033 A | 7/1992 | Ferrara et al. | |
| 5,153,827 A | 10/1992 | Courte et al. | |
| 5,169,389 A | 12/1992 | Kriesel | |
| 5,180,896 A | 1/1993 | Gibby et al. | |
| 5,184,613 A | 2/1993 | Mintz | |
| 5,186,057 A | 2/1993 | Everhart | |
| 5,195,976 A | 3/1993 | Swenson | |

| | | | | | | |
|---|---|---|---|---|---|---|
| 5,205,820 A | 4/1993 | Kriesel | | 5,755,275 A | 5/1998 | Rose et al. |
| 5,211,631 A | 5/1993 | Sheaff | | 5,772,409 A | 6/1998 | Johnson |
| 5,232,439 A | 8/1993 | Campbell et al. | | 5,788,669 A | 8/1998 | Peterson |
| 5,241,951 A | 9/1993 | Mason et al. | | 5,788,671 A | 8/1998 | Johnson |
| 5,243,833 A | 9/1993 | Coelho et al. | | 5,805,455 A | 9/1998 | Lipps |
| 5,245,693 A | 9/1993 | Ford et al. | | 5,806,528 A | 9/1998 | Magliochetti |
| 5,250,032 A | 10/1993 | Carter, Jr. et al. | | 5,807,332 A | 9/1998 | Augustine et al. |
| 5,254,094 A | 10/1993 | Starkey et al. | | 5,810,771 A | 9/1998 | Blomquist |
| 5,261,411 A | 11/1993 | Hughes | | 5,816,797 A | 10/1998 | Shoenfeld |
| 5,261,875 A | 11/1993 | Spears et al. | | 5,823,746 A | 10/1998 | Johnson |
| 5,263,323 A | 11/1993 | Maus et al. | | 5,824,000 A | 10/1998 | Pavlo et al. |
| 5,263,929 A | 11/1993 | Falcone et al. | | 5,829,880 A | 11/1998 | Diedrich |
| 5,269,749 A | 12/1993 | Koturov | | 5,840,068 A | 11/1998 | Cartledge |
| 5,279,558 A | 1/1994 | Kriesel | | 5,862,672 A | 1/1999 | Faries, Jr. et al. |
| 5,279,598 A | 1/1994 | Sheaff | | 5,875,282 A | 2/1999 | Jordan et al. |
| 5,282,264 A | 1/1994 | Reeves et al. | | 5,876,370 A | 3/1999 | Blomquist |
| 5,290,222 A | 3/1994 | Feng et al. | | 5,879,143 A | 3/1999 | Cote et al. |
| 5,290,230 A | 3/1994 | Ainsworth et al. | | 5,879,329 A | 3/1999 | Ginsburg |
| 5,297,234 A | 3/1994 | Harms et al. | | 5,891,096 A | 4/1999 | Hyun et al. |
| 5,308,335 A | 5/1994 | Ross et al. | | 5,893,843 A | 4/1999 | Rodrigues |
| 5,318,540 A | 6/1994 | Athayde et al. | | 5,919,218 A | 7/1999 | Carr |
| 5,330,431 A | 7/1994 | Herskowitz | | 5,928,196 A | 7/1999 | Johnson et al. |
| 5,338,157 A | 8/1994 | Blomquist | | 5,935,099 A | 8/1999 | Peterson et al. |
| 5,342,313 A | 8/1994 | Campbell et al. | | 5,935,106 A | 8/1999 | Olsen |
| 5,348,539 A | 9/1994 | Herskowitz | | 5,954,485 A | 9/1999 | Johnson et al. |
| 5,364,371 A | 11/1994 | Kamen | | 5,954,700 A | 9/1999 | Kovelman |
| 5,364,385 A | 11/1994 | Harms et al. | | 5,961,492 A | 10/1999 | Kriesel et al. |
| 5,370,674 A | 12/1994 | Farrell | | 5,961,700 A | 10/1999 | Oliver |
| 5,381,510 A | 1/1995 | Ford et al. | | 5,961,866 A | 10/1999 | Hansen |
| 5,389,078 A | 2/1995 | Zalesky et al. | | 5,986,239 A | 11/1999 | Corrigan, III et al. |
| 5,392,025 A | 2/1995 | Figh et al. | | 5,989,238 A | 11/1999 | Ginsburg |
| 5,397,875 A | 3/1995 | Bechtold, Jr. | | 6,024,539 A | 2/2000 | Blomquist |
| 5,399,007 A | 3/1995 | Marconet | | 6,035,102 A | 3/2000 | Bakke |
| 5,399,166 A | 3/1995 | Laing | | 6,045,648 A | 4/2000 | Palmgren et al. |
| 5,408,576 A | 4/1995 | Bishop | | 6,062,429 A | 5/2000 | West et al. |
| 5,408,577 A | 4/1995 | Weber, Jr. et al. | | 6,096,007 A | 8/2000 | Haan et al. |
| 5,411,480 A | 5/1995 | Kriesel | | 6,117,122 A | 9/2000 | Din et al. |
| 5,411,482 A | 5/1995 | Campbell | | 6,129,702 A | 10/2000 | Woias et al. |
| 5,417,274 A | 5/1995 | Verkaart | | 6,139,528 A | 10/2000 | Kristher et al. |
| 5,420,962 A | 5/1995 | Bakke | | 6,142,974 A | 11/2000 | Kristher et al. |
| 5,423,759 A | 6/1995 | Campbell | | 6,146,359 A | 11/2000 | Carr et al. |
| 5,433,704 A | 7/1995 | Ross et al. | | 6,158,458 A | 12/2000 | Ryan |
| 5,451,209 A | 9/1995 | Ainsworth et al. | | 6,174,300 B1 | 1/2001 | Kriesel et al. |
| 5,474,538 A | 12/1995 | Stihler et al. | | 6,175,688 B1 | 1/2001 | Cassidy et al. |
| 5,485,408 A | 1/1996 | Blomquist | | 6,221,045 B1 | 4/2001 | Duchon et al. |
| 5,492,534 A | 2/1996 | Athayde et al. | | 6,221,051 B1 | 4/2001 | Hjertman et al. |
| 5,494,196 A | 2/1996 | Tyner | | 6,236,809 B1 | 5/2001 | Cassidy et al. |
| 5,512,043 A | 4/1996 | Verkaart | | 6,248,077 B1 | 6/2001 | Elson et al. |
| 5,514,095 A | 5/1996 | Brightbill et al. | | 6,254,572 B1 | 7/2001 | Knipfer et al. |
| 5,531,697 A | 7/1996 | Olsen et al. | | 6,261,261 B1 | 7/2001 | Gordon |
| 5,531,698 A | 7/1996 | Olsen | | 6,315,767 B1 | 11/2001 | Dumont et al. |
| 5,538,399 A | 7/1996 | Johnson | | 6,316,750 B1 | 11/2001 | Levin |
| 5,540,561 A | 7/1996 | Johnson | | 6,334,707 B1 | 1/2002 | Ku |
| 5,564,915 A | 10/1996 | Johnson | | 6,371,121 B1 | 4/2002 | Faries, Jr. et al. |
| 5,567,119 A | 10/1996 | Johnson | | 6,464,666 B1 | 10/2002 | Augustine |
| 5,567,136 A | 10/1996 | Johnson | | 6,467,953 B1 | 10/2002 | Faries, Jr. et al. |
| 5,572,873 A | 11/1996 | Lavigne et al. | | 6,480,257 B2 | 11/2002 | Cassidy et al. |
| 5,584,811 A | 12/1996 | Ross et al. | | 6,524,239 B1 | 2/2003 | Reed et al. |
| 5,590,648 A | 1/1997 | Mitchell | | 6,553,336 B1 | 4/2003 | Johnson et al. |
| 5,609,784 A | 3/1997 | Davenport | | 6,566,631 B2 | 5/2003 | Faries, Jr. et al. |
| RE35,501 E | 5/1997 | Ross et al. | | 6,641,602 B2 | 11/2003 | Balding |
| 5,647,854 A | 7/1997 | Olsen et al. | | 6,649,040 B1 | 11/2003 | Mirchi et al. |
| 5,649,910 A | 7/1997 | Kriesel et al. | | 6,660,974 B2 | 12/2003 | Faries, Jr. et al. |
| 5,658,250 A | 8/1997 | Blomquist et al. | | 6,722,782 B2 | 4/2004 | Faries, Jr. et al. |
| 5,658,252 A | 8/1997 | Johnson | | 6,736,788 B1 | 5/2004 | Mongomery et al. |
| 5,662,611 A | 9/1997 | Beiser et al. | | 6,740,059 B2 | 5/2004 | Flaherty |
| 5,669,877 A | 9/1997 | Blomquist | | 6,748,164 B1 | 6/2004 | Kuzyk |
| 5,681,284 A | 10/1997 | Herskowitz | | 6,768,085 B2 | 7/2004 | Faries, Jr. et al. |
| 5,683,381 A | 11/1997 | Carr et al. | | 6,788,885 B2 | 9/2004 | Mitsunaga |
| 5,690,614 A | 11/1997 | Carr et al. | | 6,788,997 B1 | 9/2004 | Frederick |
| 5,695,473 A | 12/1997 | Olsen | | 6,824,528 B1 | 11/2004 | Faries, Jr. et al. |
| 5,707,151 A | 1/1998 | Parker et al. | | 6,850,252 B1 | 2/2005 | Hoffberg |
| 5,707,431 A | 1/1998 | Verkaart et al. | | 6,860,271 B2 | 3/2005 | Faries, Jr. et al. |
| 5,713,864 A | 2/1998 | Verkaart | | 6,869,538 B2 | 3/2005 | Yu et al. |
| 5,720,728 A | 2/1998 | Ford | | 6,967,575 B1 | 11/2005 | Dohrmann et al. |
| 5,729,653 A | 3/1998 | Magliochetti et al. | | 7,031,602 B2 | 4/2006 | Faries et al. |
| 5,733,263 A | 3/1998 | Wheatman | | 7,031,778 B2 | 4/2006 | Hsiung et al. |
| 5,743,878 A | 4/1998 | Ross et al. | | 7,041,941 B2 | 5/2006 | Faries et al. |
| 5,744,806 A | 4/1998 | Frojd | | 7,090,658 B2 * | 8/2006 | Faries et al. .......... 604/113 |

| | | |
|---|---|---|
| 7,176,030 B2 | 2/2007 | Faries et al. |
| 7,238,171 B2 | 7/2007 | Faries et al. |
| 7,262,698 B1 | 8/2007 | Frederick et al. |
| 7,276,675 B2 | 10/2007 | Faries et al. |
| 7,417,205 B2 | 8/2008 | Faries, Jr. et al. |
| 7,540,864 B2 | 6/2009 | Faries, Jr. et al. |
| 7,611,504 B1 | 11/2009 | Faries, Jr. et al. |
| 7,726,876 B2 * | 6/2010 | Laverdiere et al. ............ 374/125 |
| 7,740,611 B2 | 6/2010 | Faries, Jr. et al. |
| 7,942,851 B2 | 5/2011 | Faries, Jr. et al. |
| 2001/0009610 A1 | 7/2001 | Augustine |
| 2002/0041621 A1 | 4/2002 | Faries, Jr. et al. |
| 2002/0081109 A1 | 6/2002 | Mitsunaga et al. |
| 2002/0156451 A1 * | 10/2002 | Lenker ............................ 604/500 |
| 2003/0000939 A1 | 1/2003 | Faries, Jr. et al. |
| 2003/0004470 A1 * | 1/2003 | Hickerson et al. ............ 604/251 |
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0222933 A1 | 12/2003 | Choi |
| 2003/0231990 A1 | 12/2003 | Faries, Jr. et al. |
| 2004/0170409 A1 | 9/2004 | Faries, Jr. et al. |
| 2004/0189258 A1 | 9/2004 | Lehmann et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0242930 A1 | 11/2005 | Nicolson et al. |
| 2006/0020255 A1 | 1/2006 | Cassidy et al. |
| 2006/0253075 A1 | 11/2006 | Faries, Jr. et al.. |
| 2007/0000910 A1 | 1/2007 | Faries, Jr. et al. |
| 2007/0106243 A1 | 5/2007 | Faries, Jr. et al. |
| 2007/0142773 A1 * | 6/2007 | Rosiello et al. ................ 604/113 |
| 2007/0161952 A1 | 7/2007 | Faries, Jr. et al. |
| 2007/0215018 A1 | 9/2007 | Faries, Jr. et al. |
| 2008/0021392 A1 | 1/2008 | Lurvey et al. |
| 2008/0147016 A1 | 6/2008 | Faries et al. |
| 2008/0205481 A1 | 8/2008 | Faries et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2012/0053518 A1 | 3/2012 | Faries, Jr. et al. |

FOREIGN PATENT DOCUMENTS

| | | |
|---|---|---|
| FR | 2711393 A1 | 4/1995 |
| FR | 2786057 A1 | 5/2000 |
| GB | 2029677 | 3/1980 |
| WO | 9221272 | 12/1992 |
| WO | 9838953 | 9/1998 |
| WO | 9845658 | 10/1998 |
| WO | 9922786 | 5/1999 |
| WO | 9926690 | 6/1999 |
| WO | 9958177 | 11/1999 |

OTHER PUBLICATIONS

Minco Products, Inc., Bulletin CTI98, 1996.
Eurotherm Controls, Inc., Model 2116 Temperature Controller, 1997.
Ellenwood, Drop Detector, IBM Technical Bulletin, vol. 12, No. 5, Oct. 1969.
CBi Medical, Inc., IV Fluid Warmer Model 8362, 1992.

* cited by examiner

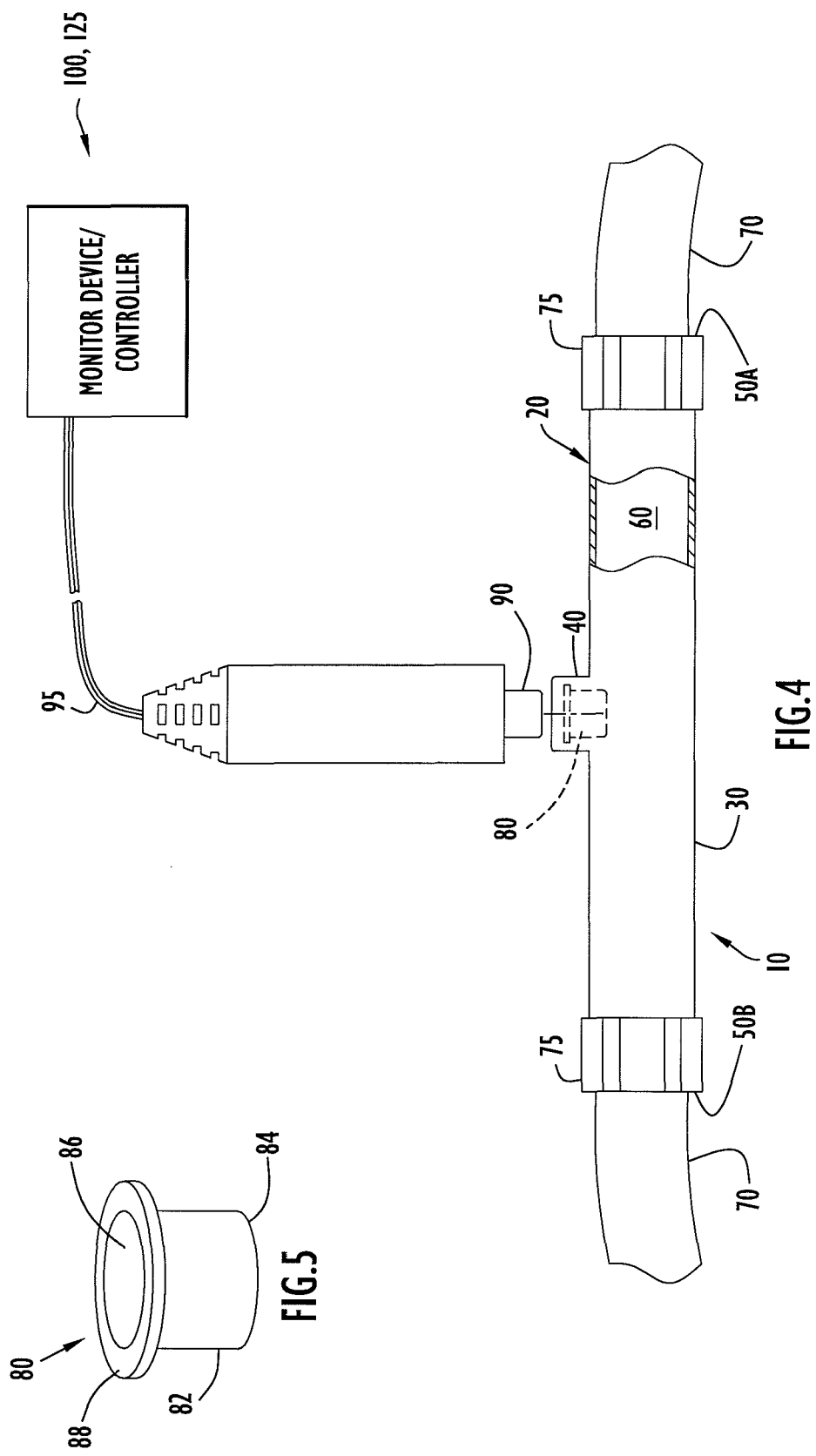

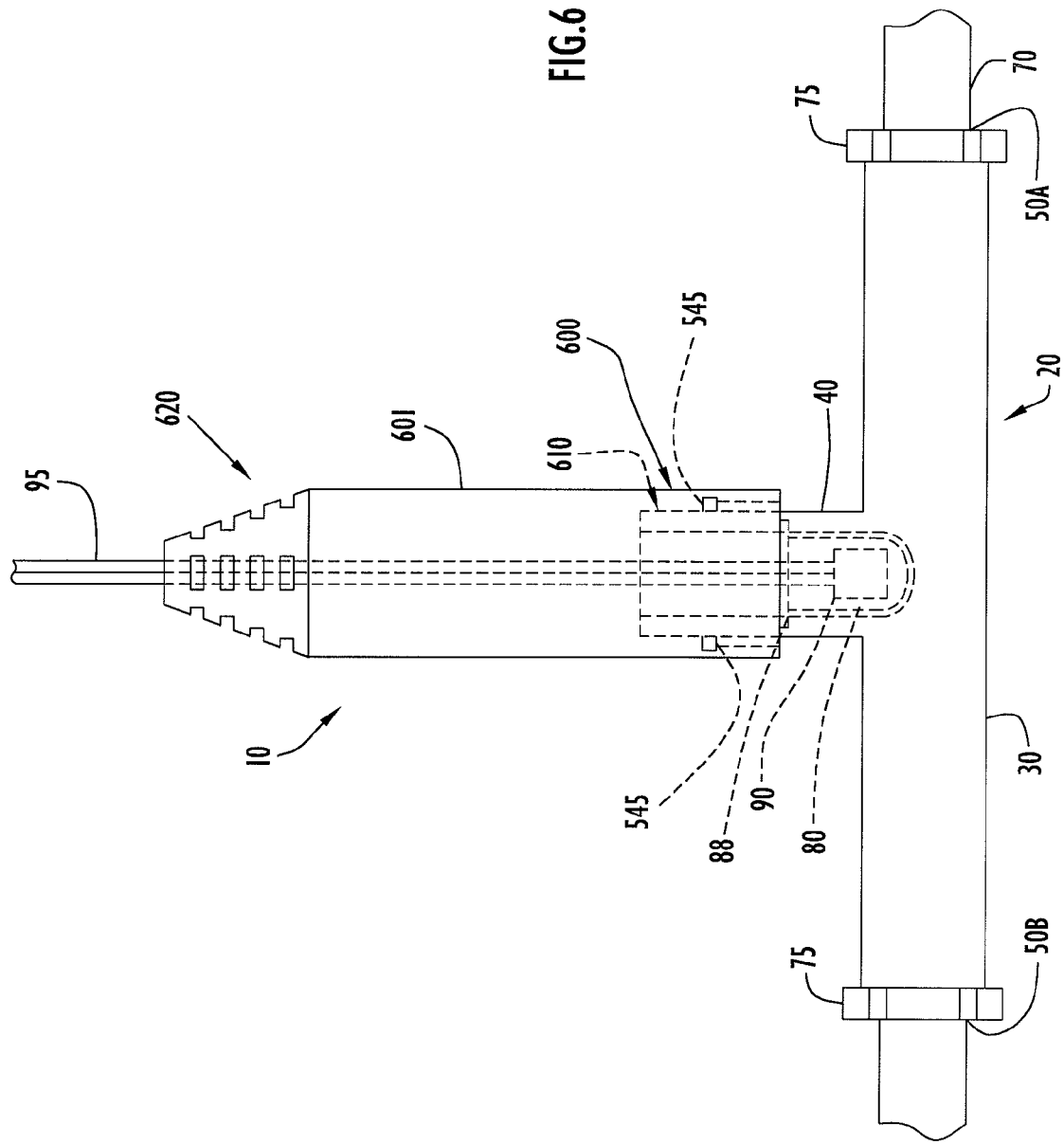

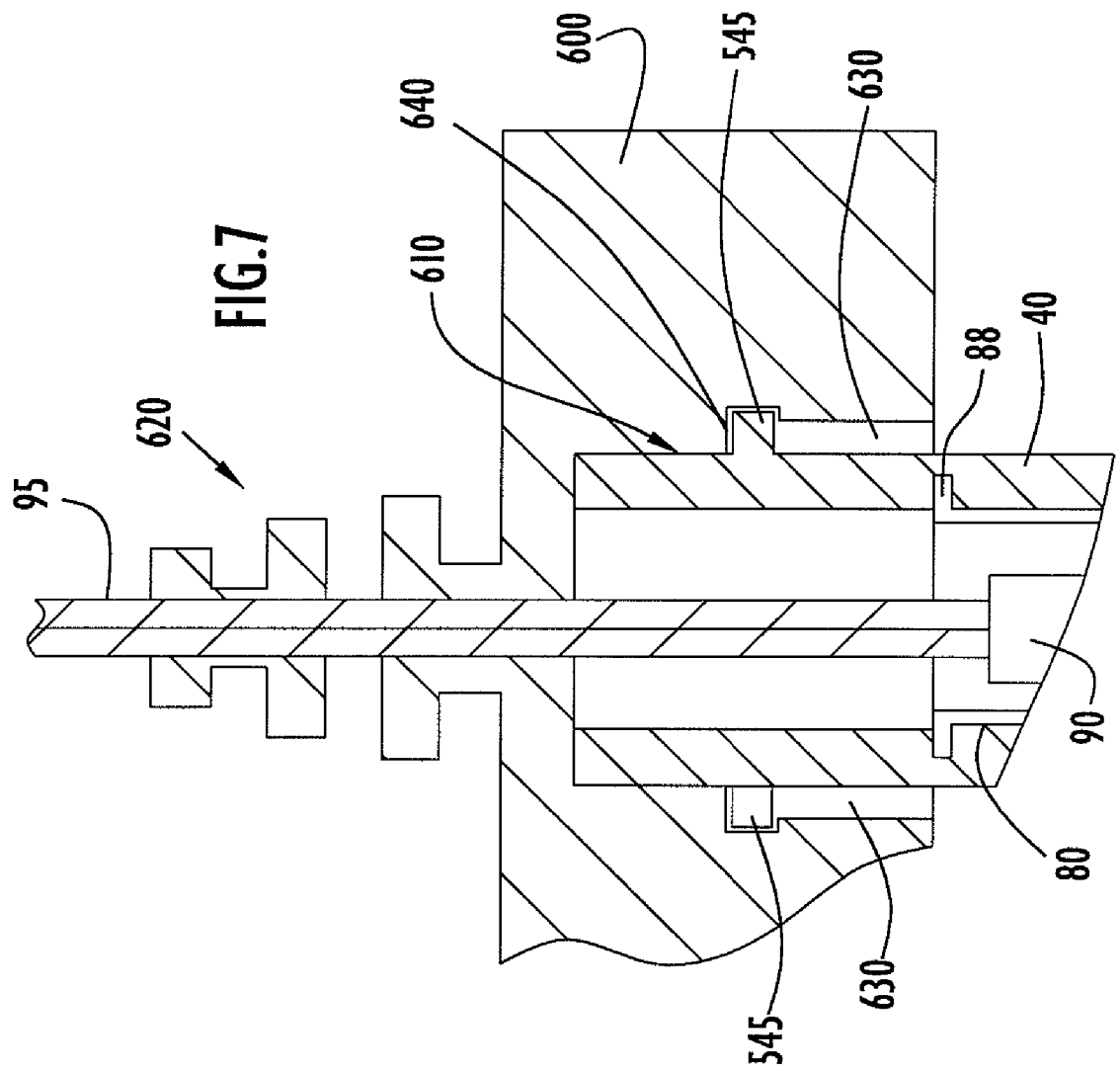

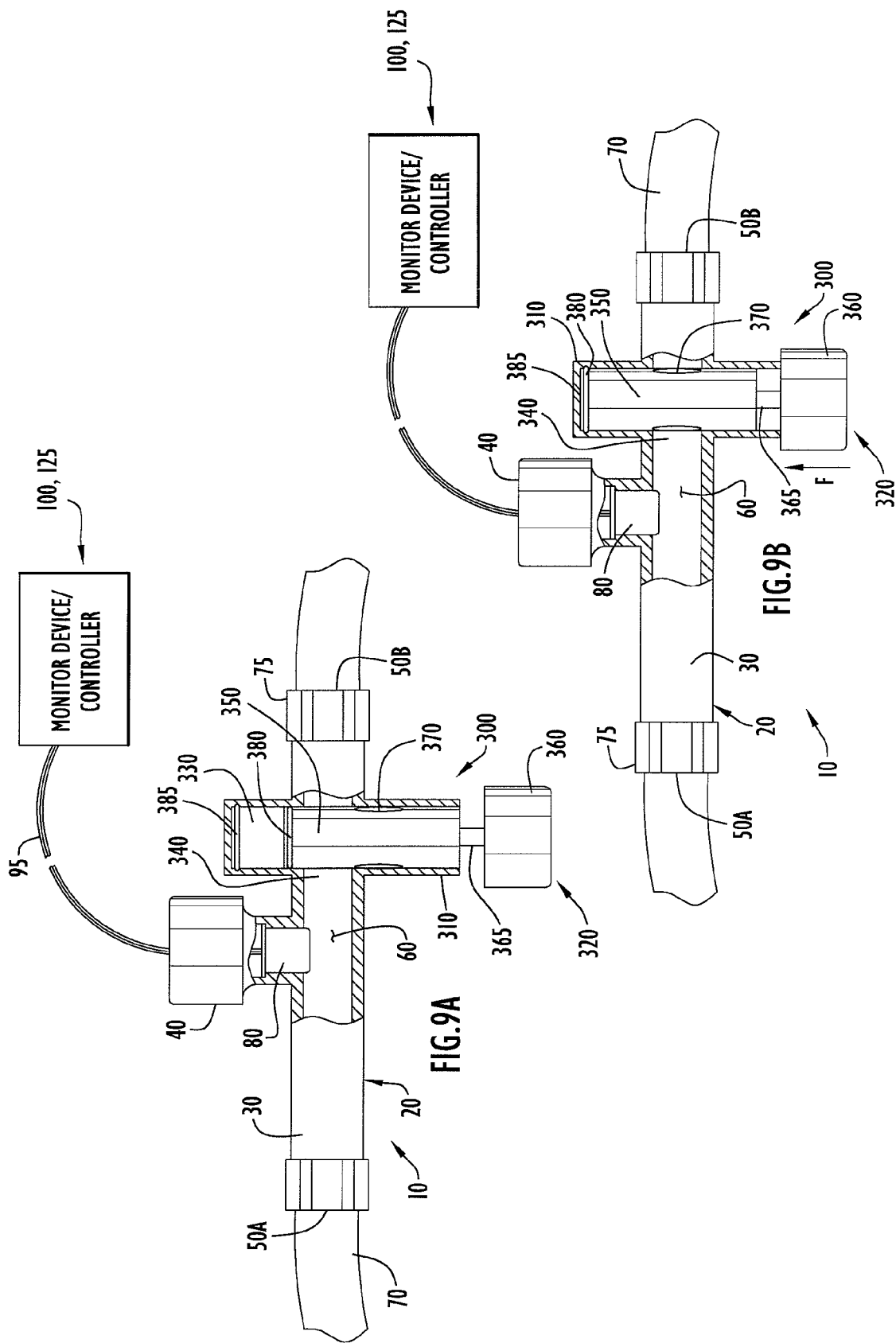

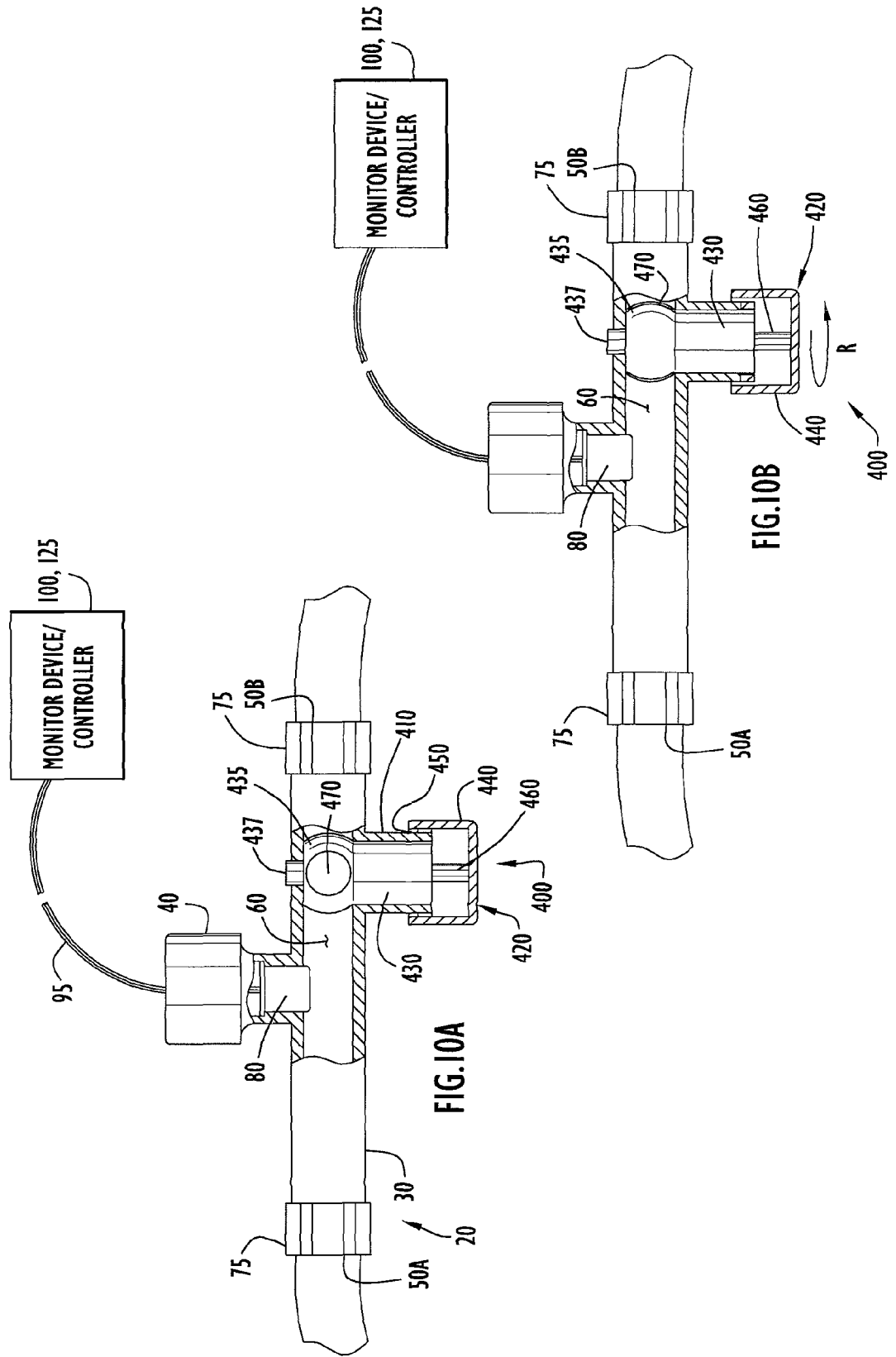

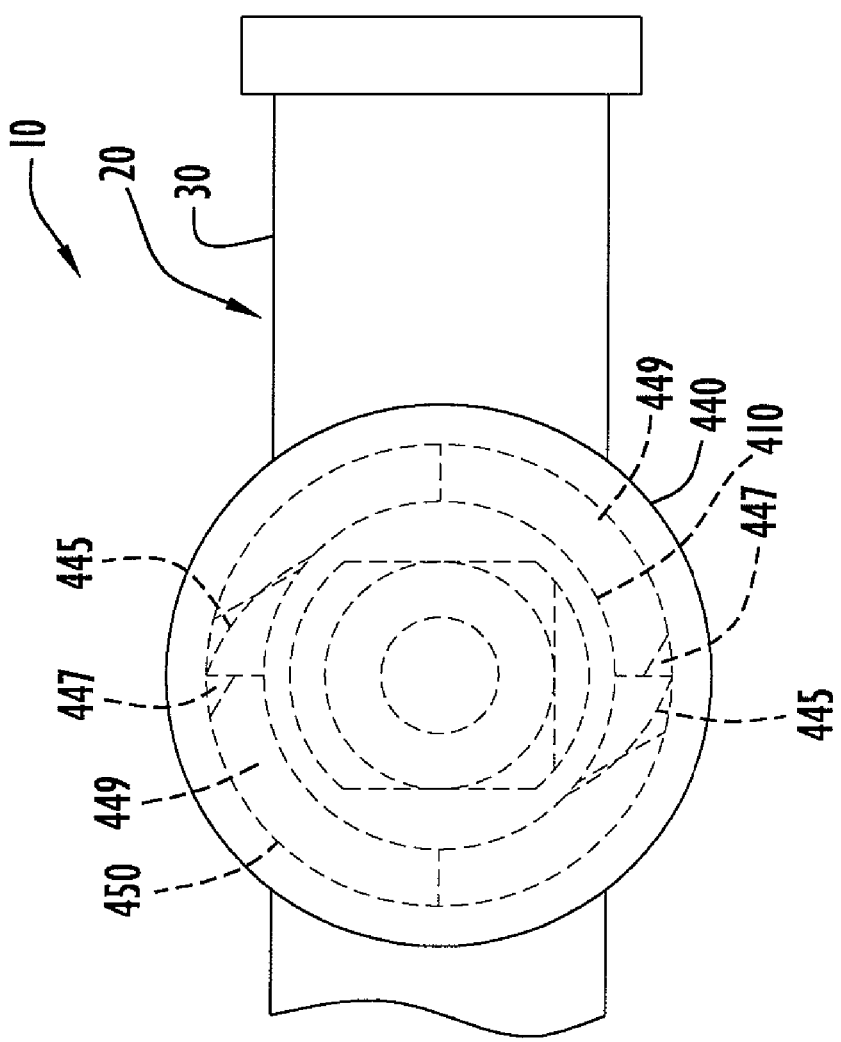

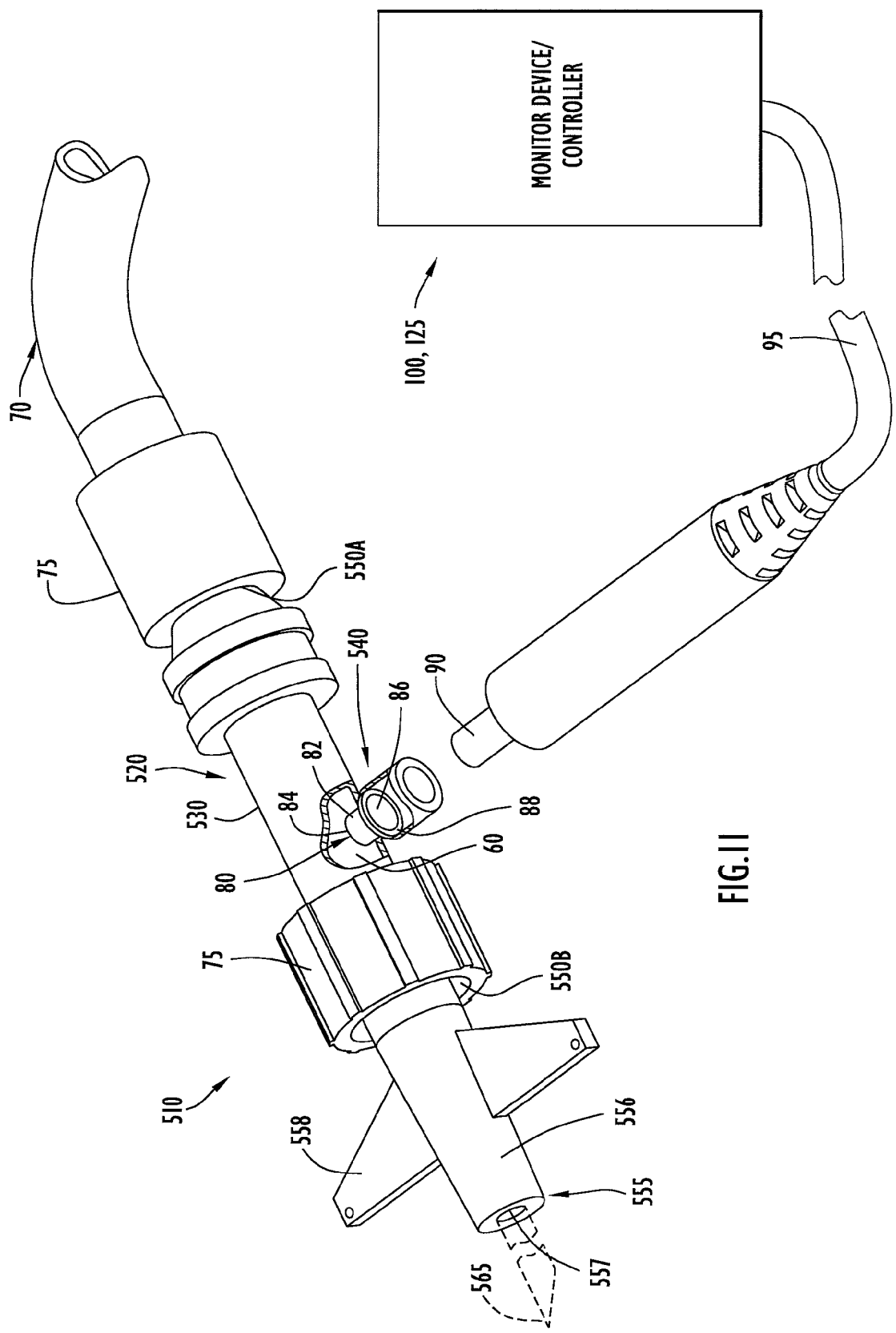

METHOD AND APPARATUS FOR MEASUREMENT AND CONTROL OF TEMPERATURE FOR INFUSED LIQUIDS

BACKGROUND OF THE INVENTION

1. Technical Field

The present invention pertains to temperature sensing devices, such as the types of temperature sensing devices disclosed in: U.S. patent application Ser. No. 10/849,251, entitled "Temperature Sensing Device for Selectively Measuring Temperature at Desired Locations Along an Intravenous Fluid Line" and filed May 20, 2004, now U.S. Patent Application Publication No. 2004/0249336 (Faries, Jr. et al.); U.S. Pat. No. 7,090,658 (Faries, Jr. et al.); and U.S. Pat. No. 6,824,528 (Faries, Jr. et al.). The disclosures of the foregoing patents and patent application publication are incorporated herein by reference in their entireties. In particular, the present invention pertains to devices that monitor temperature of an intravenous fluid at any desirable location along a fluid line (e.g., an intravenous (IV) fluid line) and may further selectively enable and/or disable the flow of fluid through those devices to ensure a desired fluid temperature is attained within the fluid line prior to entering a patient.

2. Discussion of Related Art

A patient is typically infused with intravenous (IV) fluids utilizing a liquid filled bag or container and an IV fluid line that delivers fluids under gravity and/or applied pressure from the container to the patient. It is important in many situations to maintain the temperature of the fluid in the IV line within a desirable and safe temperature range upon entering the patient so as to eliminate any potential for thermal shock and injury to the patient by the fluid.

Accordingly, the related art provides several devices that employ temperature sensors to monitor and/or control the temperature of fluid flowing within an intravenous or other type of fluid line. For example, U.S. Pat. No. 5,729,653 (Magliochetti et al.) discloses a device for heating a fluid to a body temperature prior to delivery of the fluid to a patient. In one embodiment, a fluid to be warmed prior to delivery to a patient can be passed through a flow through chamber disposed in the fluid delivery line. An electrically resistive heating element for heating the fluid can be molded into the chamber to heat the fluid from room or ambient storage temperatures to a body temperature of the patient. A probe of a temperature monitoring element can be used to monitor the temperature of the fluid exiting the chamber. In another embodiment, this information can be relayed back to a controller for controlling the power to the resistance element, and hence, the temperature of the fluid. In still another embodiment, an infrared temperature sensor can be used for monitoring the temperature of the fluid exiting the chamber by scanning through a window in the chamber outlet port or elsewhere in the fluid line. The device may further include an LED two-digit display of the exiting fluid temperature for visual temperature monitoring.

U.S. Pat. No. 5,250,032 (Carter, Jr. et al.) discloses a heater for warming blood, plasma and other solutions flowing through an IV tube prior to entry into a patient. The heater is releasably secured to a patient and includes a housing having an elongated channel extending from one end of the housing to its other end. The channel is formed with an elongated slot against which a heating element is mounted. The heating element is controlled by a control circuit and powered by batteries. The control circuit may energize the heating element continuously or cyclically in response to sensed temperatures.

U.S. Pat. No. 3,526,134 (Schaus) discloses a thermobulb mount for holding a temperature sensing element in a pipeline so as to prevent damage to the element which might otherwise be caused by fluid flow within the pipeline. The mount includes a body having threaded ends for connection in series with a pipeline, an installation boss with a hole through which the sensing element extends and a recess formed on the inside of the pipeline opposite the boss for supporting an outboard end of the sensing element.

U.S. Pat. No. 5,829,880 (Diedrich) discloses a device including a T-type pipe combination including a medium conduction pipe and a connection piece projecting away from the pipe. The pipe is connected to tubing that supplies medium to and leads medium away from the pipe. A plug unit is disposed within the connection piece and includes a stopper supporting contact pins, as well as a temperature sensor connected to those pins. The temperature sensor indirectly measures the temperature of the medium flowing through the pipe. An electrical bush part is further secured to the connection piece via a bracket and is connected to the contact pins. The bush part housing includes contact bushes with electrical connecting lines that extend externally of the housing through openings defined therein.

U.S. Pat. No. 4,138,890 (Brown) discloses a temperature indicating probe including a liquid-in-glass thermometer encased within a housing. The housing includes a series of tapered, cylindrical shaped portions separated by a step or shoulder, which are respectively insertable into variously sized standard medical appliance line openings or fittings, for sensing and indicating the temperature of the working fluids being carried through the line.

U.S. Pat. No. 4,476,877 (Barker) discloses a temperature sensing device for use in a fluid flow system. The device includes a housing with a tapered lumen extending through the housing, an opening extending through the housing and a thermally conductive enclosure inserted within the opening. The thermally conductive enclosure extends substantially fully across the lumen. A thermistor temperature sensor is potted in a carrier to be received within the enclosure in order to determine the temperature of injectate flowing from a syringe through the lumen. The measured temperature is utilized to determine desired blood flow rate information.

U.S. Pat. Nos. 6,248,077 and 6,336,902 (Elson et al.) disclose a system for sensing a characteristic of fluid flowing to or from a human body comprising a conduit having a first end adapted to be outside the body, a second end adapted to be received within the body, a flow passage through which fluid can flow between the first and second ends and a probe including a sensor for sensing a characteristic of the fluid. The probe is mounted on the conduit with the sensor in the flow passage. The sensor is isolated from the fluid flowing in the flow passage.

The related art suffers from several disadvantages. In particular, the Magliochetti et al. and Carter, Jr. et al. systems have size and/or mounting requirements that tend to restrict system application to particular sections of an IV line. Thus, operators are required to estimate, or adjust system settings to compensate for, conditions at desired IV line sites outside the system application range. This may lead to inaccuracies in fluid temperature control and measurement for the desired sites, thereby risking injury to a patient. In addition, the Carter, Jr. et al. system measures temperature for temperature control of fluid without providing any temperature indication to an operator, thereby enabling infusion of fluid of unknown temperature into a patient.

The Schaus and Diedrich devices are designed for non-medical fluid systems. Accordingly, these devices are employed for non-sterile applications and are ill-suited for medical applications that require sterility. Although these devices measure fluid temperature, the devices generally do not provide a displayed temperature to an operator. Thus, fluids may attain inappropriate temperatures without notice to the operator which may lead to undesirable conditions or consequences. The Brown device requires an operator to manually observe a thermometer and determine a fluid temperature therefrom. This is distracting to the operator and permits possible operator error to be introduced with respect to the fluid temperature measurement, thereby enabling infusion of fluid at an inappropriate temperature and risking injury to the patient.

The Elson et al. (U.S. Pat. Nos. 6,248,077 and 6,336,902) and Barker systems do not provide temperature control of the fluid, or a manner within the line to control the fluid flow. This may enable infusion of a fluid at an inappropriate temperature into a patient, thereby increasing the risk of injury.

OBJECTS AND SUMMARY OF THE INVENTION

Accordingly, it is an object of the present invention to measure the temperature of a fluid within an IV line via a temperature sensing device that is selectively securable to any desired site along the line.

It is another object of the present invention to obtain an accurate and reliable temperature indication of fluid within an IV line at any desired location along that line and display the temperature indication to an operator.

Yet another object of the present invention is to removably secure a temperature sensing device to an IV line and facilitate measurement of fluid temperatures at varying locations along that line.

Still another object of the present invention is to facilitate re-use of a temperature sensor with a temperature sensing device to measure the temperature of fluid within an IV line while maintaining sterility of that fluid.

A further object of the present invention is to measure and display the temperature of fluid within an IV line via a line fitting employing a temperature sensor coupled to a display device.

Yet another object of the present invention is to control the temperature of fluid flowing within an IV line based on a temperature measurement of that fluid within the line.

Still another object of the present invention is to control fluid flow within an IV line to ensure the fluid attains a desired temperature prior to infusion into a patient.

A further object of the present invention is to control fluid flow along an IV line using a valve that selectively obstructs the fluid flow path.

The aforesaid objects may be achieved individually and/or in combination, and it is not intended that the present invention be construed as requiring two or more of the objects to be combined unless expressly required by the claims attached hereto.

According to present invention embodiments, a device measures the temperature of fluid within an IV line at selected locations along that line. The device is securable to any desired portions of the IV line and includes a temperature sensor for measuring fluid flowing within the desired line portion. The device may be in the form of a fitting including a fluid channel and a projection in fluid communication with the fluid channel to receive a temperature sensor for a temperature measurement. A thermally conductive receptacle configured to receive the temperature sensor may be disposed in the projection. The conductive receptacle partially extends into the fluid channel for direct contact with the fluid to enable temperature measurement by the temperature sensor. The temperature sensor may be coupled to a temperature display device and/or controller to respectively display the measured temperature and/or control a thermal element to regulate temperature of the fluid within the line.

The fitting may further include a control valve that controls the flow of fluid through the fluid channel. The control valve may be in the form of a plunger-type mechanism, where a piston may be manipulated linearly to adjust the position of a piston aperture relative to the fluid channel to control fluid flow within that channel. Alternatively, the control valve may be configured as a rotation-type mechanism, where the piston is manipulated rotationally to adjust the position of the piston aperture relative to the fluid channel. The control valve may be employed to prevent fluid flow until the fluid attains an appropriate temperature for infusion into a patient. In addition, the device may further be connected to, or be in the form of, a needle hub to measure fluid temperature proximate the entry site on a patient.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 4 is a view in perspective of a temperature sensing device for an IV fluid line including a fitting with a thermally conductive receptacle for receiving a temperature sensor according to an embodiment of the present invention.

FIG. 5 is a view in perspective of the receptacle utilized in the fitting of FIG. 4.

FIG. 6 is a view in perspective of a locking mechanism securing a temperature sensor to the temperature sensing device of FIG. 4.

FIG. 7 is a view in elevation and section of the locking mechanism of FIG. 6 securing the temperature sensor to the temperature sensing device.

FIGS. 9A-9C are perspective views of a temperature sensing device including a plunger-type fluid flow control mechanism according to embodiments of the present invention.

FIGS. 10A-10D are perspective views of a temperature sensing device including a rotation-type fluid flow control mechanism according to embodiments of the present invention.

FIG. 11 is a view in perspective of a temperature sensing device measuring temperature of fluid proximate an entry site of a patient according to an embodiment of the present invention.

DETAILED DESCRIPTION OF THE PREFERRED EMBODIMENTS

Figure 1:
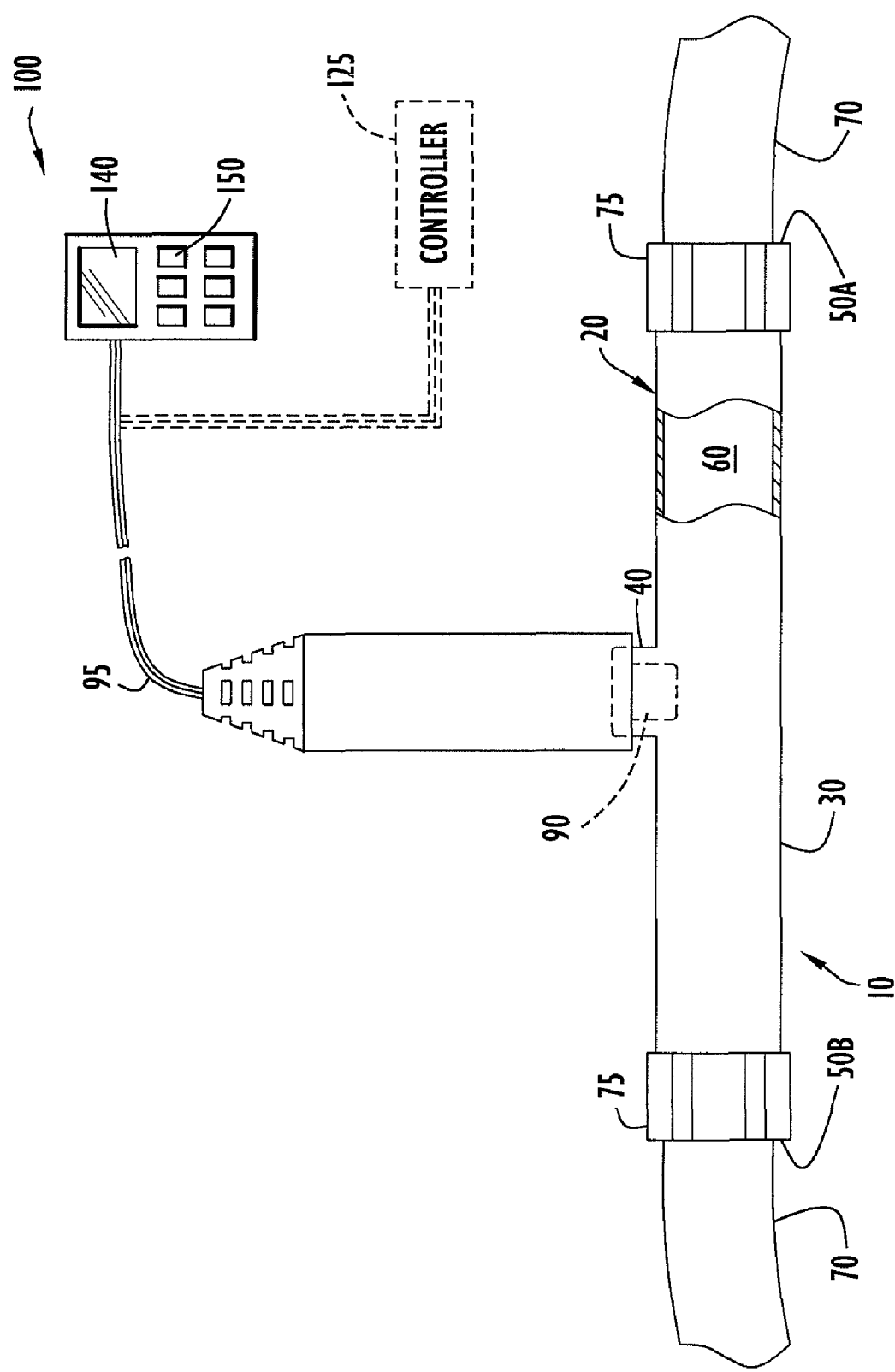
FIG. 1 is a view in perspective of a temperature sensing device in the form of a line fitting according to an embodiment of the present invention.

A temperature sensing device for measuring the temperature of a fluid within an intravenous (IV) or other medical fluid line at desired locations along that line according to an embodiment of the present invention is illustrated in FIG. 1. Specifically, temperature sensing device 10 may be in the form of a fitting 20 including a base portion 30 and a projection 40 extending transversely from an intermediate section of the base portion. By way of example only, the fitting includes a T-type configuration; however, any suitable configuration (e.g., a Y-type fitting, cross fitting, coupling, etc.) may be utilized. Base portion 30 is substantially cylindrical with a first open end 50A, a second open end 50B, and a channel or fluid conduit 60 defined longitudinally through the base portion to permit fluid flow through the fitting. Base portion channel 60 preferably includes generally uniform dimensions; however, the channel dimensions may vary along the channel (e.g., the channel dimensions may fluctuate or progressively increase or decrease between open ends 50A, 50B). In addition, the base portion, projection and channel may alternatively be of any suitable size or shape.

First open end 50A is preferably connected to a corresponding segment of an IV line 70 coupled to a fluid source, while second open end 50B is typically secured to a corresponding IV line segment coupled to an entry site on a patient. Open ends 50A, 50B are preferably removably secured to selected portions of IV line 70 via Luer locks or other connectors 75. However, the fitting open ends may be secured to the IV line segments via any conventional or other techniques (e.g., friction fit arrangement, clamps, brackets, connectors, etc.).

Fitting 20 is typically removed from IV line 70 and replaced after each use to ensure sterility of the fluid. Alternatively, fitting 20 may be permanently secured to IV line 70 (e.g., by adhering or welding ends 50A, 50B of the fitting to portions of the IV line) to form a disposable IV line set. Fitting 20 may be constructed of plastic or any other rigid material suitable for use with IV lines.

Projection 40 serves to securely position a temperature sensor or probe 90 within fitting 20 with at least a portion of the temperature sensor in thermal relation with fluid flowing through fluid channel 60. Projection 40 is generally cylindrical and includes open ends to facilitate access to fluid channel 60. Temperature sensor 90 is inserted into projection 40 and partially extends within fluid channel 60 for direct contact with fluid flowing within that channel. Temperature sensor 90 may be implemented by any conventional or other temperature sensor (e.g., RTD, IR, NTC, thermistor, thermocouple, etc.) and may be secured within the projection via any securing mechanisms (e.g., friction fit, adhesives, etc.).

Temperature sensor 90 is disposed within projection 40 in a manner that provides a fluid tight seal with base portion channel 60 to maintain IV fluid within fitting 20. By way of example, temperature sensor 90 may include threads configured to mate with complementary threads on projection 40 to provide a quick attachment/detachment mechanism and assure that the temperature sensor is properly seated in the projection. Sensor wiring 95 may connect temperature sensor 90 to a monitor device 100 to display the measured temperature, or to a controller 125 that controls thermal treatment devices or elements to thermally treat the fluid within IV line 70 to a desired temperature.

Figure 2:
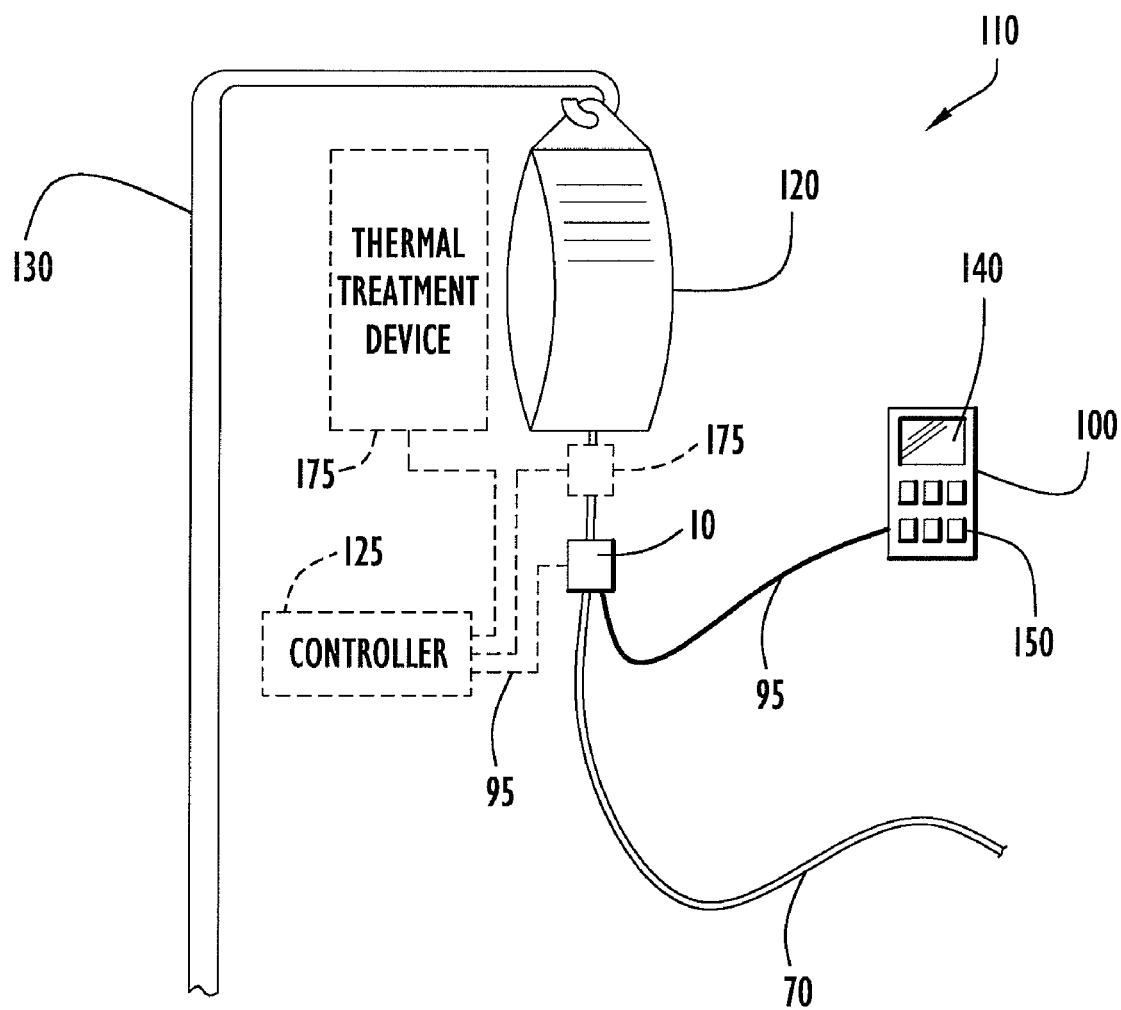
FIG. 2 is a view in perspective of the temperature sensing device of FIG. 1 employed with an infusion apparatus.

Temperature sensing device 10 may be disposed along IV line 70 of an infusion apparatus as illustrated in FIG. 2. Specifically, an infusion apparatus 110 includes an IV pole 130, a solution bag 120 suspended therefrom and IV line 70 enabling flow of solution from the solution bag to a patient. Temperature sensing device 10 may be removably affixed to any selected portion of IV line 70 for measuring the temperature of fluid within the IV fluid line. The infusion apparatus may further include monitor device 100 in communication with temperature sensing device 10 via sensor wiring 95. Monitor device 100 is configured to provide an operator with indications of fluid temperature measurements at operator selected locations along IV line 70. Monitor device 100 may alternatively communicate with temperature sensing device 10 in any suitable manner (e.g., electrical line, RF, IR, etc.).

Monitor device 100 typically includes a temperature display 140 (e.g., LED or LCD), one or more input devices or buttons 150, and a processor to control monitor device operation and determine fluid temperature based on signals received from temperature sensing device 10. The display typically indicates the temperature measured by temperature sensor 90, and may further indicate a desired or set-point temperature entered by the operator via buttons 150. The monitor device may further provide an indication when the temperature measured by temperature sensing device 10 falls within (or outside) a desired range of the set-point temperature. By way of example, the monitor device may further include audio and/or visual indicators (e.g., beeper or buzzer, speaker, various colored light emitting diodes (e.g., green diode, yellow diode and red diode), etc.) to inform an operator of the measured temperature. In addition, monitor device 100 may include a printer and/or data recorder to print and/or record data associated with the measured IV fluid temperature. Exemplary monitor devices for use with temperature sensing device 10 include a Fluke 50S hand-held thermometer available from Fluke Corporation and a printing thermometer available from Extech Instruments.

Alternatively, infusion apparatus 110 may include one or more thermal treatment devices 175, and controller 125 coupled to the thermal treatment devices and temperature sensing device 10. The thermal treatment devices may be disposed at various locations proximate solution bag 120 and/or IV line 70 to thermally treat (e.g., heat and/or cool) fluid within the solution bag and/or flowing within the IV line to a desired temperature, preferably in the range of 33°-150° F. The thermal treatment devices may be implemented by any conventional or other type of heating and/or cooling elements (e.g., pads, wires, devices employing heat exchange fluids, heating coils, cooling coils, etc.), and may thermally treat the fluid to any suitable desired temperature or temperature range. In addition, the thermal treatment devices may be of any quantity and dimensions, may include any configuration suitable for thermally treating the fluid (e.g., strips, bars, segments, etc.), and may be secured to the solution bag and/or any location along IV line 70 via any conventional or other techniques (e.g., hook and loop fasteners, brackets, receptacles, clamps, etc.). Controller 125 receives the measured temperature from temperature sensing device 10 via sensor wiring 95 and controls thermal treatment devices 175 to thermally treat (e.g., heat and/or cool) fluid within solution bag 120 and/or within IV line 70 to a desired or set-point temperature. The controller may further display the measured and/or set-point temperatures to an operator. Controller 125 may alternatively communicate with temperature sensing device 10 in any suitable manner (e.g., electrical line, RF, IR, etc.).

Figure 3:
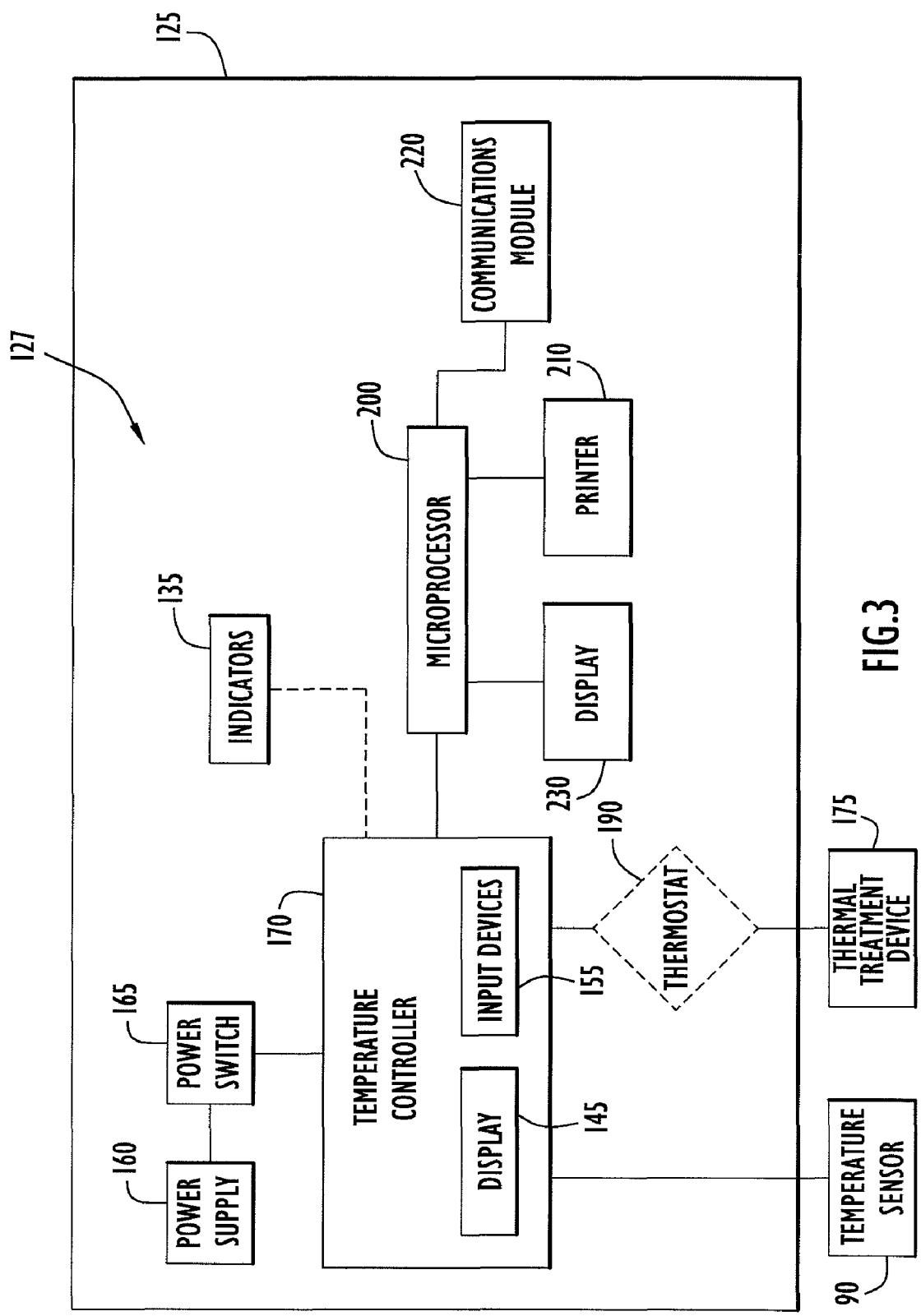
FIG. 3 is a schematic block diagram of control circuitry for controlling temperature of fluid within an IV line according to an embodiment of the present invention.

A control circuit for controller 125 according to an embodiment of the present invention is illustrated in FIG. 3. Specifically, control circuit 127 includes a power supply 160, a power switch 165, and a temperature controller 170. Power supply 160 may be implemented by any conventional or other power supply device and typically provides appropriate power signals (e.g., may receive AC or DC power signals and provide AC or DC power signals at any appropriate power levels) to the control circuit components. Power switch 165 may be implemented by any suitable switching device (e.g., button, switch, etc.) and enables power to control circuit components. Temperature controller 170 is operatively connected to thermal treatment devices 175 and temperature sensor 90. The temperature controller controls the thermal treatment devices in accordance with an operator-entered set point temperature and the temperature measured by temperature sensor 90.

Temperature controller 170 may be implemented by any conventional or other temperature controller or processor (e.g., microprocessor, controller, etc.) and includes a display 145 and input devices 155. The input devices enable entry of various information (e.g., set point or desired fluid temperature, etc.), while the display may display any desired information (e.g., measured and/or set-point temperatures, etc.).

Control circuit 127 may further include a thermostat 190 disposed between temperature controller 170 and thermal treatment devices 175. The thermostat may measure temperature of the thermal treatment devices and disable the devices in response to a temperature measurement of the devices exceeding a temperature threshold. For example, thermostat 190 may disable a thermal treatment device in the form of a heating element in response to detection of excessive heating element temperatures. The thermostat may be implemented by any conventional or other switching type or limiting devices (e.g., a high limit thermostat, etc.).

Control circuit 127 may further provide an indication when the temperature measured by temperature sensing device 10 falls within (or outside) a desired range of the set-point temperature. By way of example, the control circuit may further include audio and/or visual indicators 135 (e.g., beeper or buzzer, speaker, various colored light emitting diodes (e.g., green diode, yellow diode and red diode), etc.) to inform an operator of the measured temperature. The control circuit (e.g., temperature controller 170) may selectively actuate the indicators in any fashion to indicate a particular determined condition (e.g., a temperature beyond a desired set-point temperature, etc.).

In addition, the control circuit may include devices to measure, record and/or provide a report (e.g., hardcopy or electronic form) of system conditions (e.g., time, date, temperature, etc.). The report provides medical personnel documentation for their files on the heating (and/or cooling) characteristics. The primary information produced is the start date and start time of solution thermal treatment, the time interval the solution was thermally treated and the temperature the solution attained during thermal treatment (e.g., partial or complete history of time and solution temperature). The report may further include a variety of information (e.g., facility name and location, patient information, doctor information, type of procedure, type of solution being thermally treated, amount of solution being thermally treated, etc.).

Specifically, the control circuit may include a processor 200, a printer 210, and a communications module 220. These components may be implemented by any conventional or other components performing the functions described herein. Processor 200 is coupled to temperature controller 170 in order to receive information relating to temperature sensor 90 (e.g., the fluid temperature) and the thermal treatment device temperature. Processor 200 may receive any additional information (e.g., facility information, doctor information, patient information, solution information, instrument information, etc.) from medical personnel or users via processor input devices. The processor further maintains the date, elapsed heating and/or cooling time, and occurrence time of an event or condition (e.g., the time when a set point temperature is set or attained). Processor 200 may measure the elapsed time or record an occurrence time based on signals received from the temperature controller. For example, processor 200 may measure elapsed time or record elapsed and/or occurrence time in response to medical personnel manually entering information on the processor input devices (e.g., start and stop keys). Processor 200 collects the appropriate information and arranges the information into a report. The report may be arranged in any fashion and include any desired information. Moreover, the report and/or information may be stored in a database or memory device (e.g., local memory, removable memory, card, disk, Smart Card, USB memory device, etc.) for later retrieval. In addition, processor 200 may be coupled to a processor or system display 230 to display the elapsed (or running) time, report or any desired information to medical personnel. The information displayed may be selected via the processor input devices, or the display may include display controls (e.g., buttons, keys, etc.). System display 230 may be implemented by any conventional or other display of any shape or size and may be disposed on controller 125 at any desired location.

Processor 200 is coupled to printer 210 and communications module 220 in order to provide information to a user. Printer 210 basically provides a report in hardcopy form. The processor may control the printer to produce the report at specified times (e.g., termination of treatment, at particular times of day, after a particular quantity of uses, etc.) or in response to requests from medical personnel via processor input devices (e.g., print key). Printer 210 may print the report on any desired hardcopy medium. Preferably, the printer places the information onto a label that is attached to a medical file. The information may be printed during or after thermal treatment of the solution, or be stored on a memory device and printed at a desired time as described above. Printer 210 may further provide additional copies of the report in response to user requests, or a medium that automatically creates duplicates may be utilized (e.g., carbon-less paper, etc.).

Communications module 220 enables the report to be provided in electronic form. This module basically facilitates communication with other devices for transference or downloading of the report to those devices. For example, the information may be downloaded or transmitted over a network or other communications medium to another device (e.g., PDA, computer, a Smart Card, a USB memory drive, BLUETOOTH or other wireless technology, etc.) for viewing, storage and/or printing. Moreover, communications module 220 may facilitate retrieval of information (e.g., patient information, facility information, doctor information, solution information, instrument information, etc.) from a database or other source for the report.

Operation of temperature sensing device 10 is described with reference to FIGS. 1-3. Initially, temperature sensing device 10 is attached to IV line 70 by securing base portion open ends 50A, 50B to operator selected portions of the IV line. Sensor wiring 95 is connected to monitor device 100 for temperature display, or to controller 125 for temperature display and control. A desired or set point temperature for the fluid may be entered by an operator into the monitor device or controller. IV fluid from solution bag 120 is permitted to flow through the IV line and fitting 20. As the fluid flows through fitting 20, temperature sensor 90 contacts the fluid flowing within channel 60, thereby directly measuring the temperature of the fluid. The temperature sensor may transmit the measured temperature information via sensor wiring 95 to monitor device 100 for display of the fluid temperature on display 140. The monitor device may further actuate visual and/or audio indicators to inform an operator that the measured fluid temperature is beyond the set-point temperature or a temperature range as described above.

Alternatively, the temperature sensor may transmit the measured temperature information via sensor wiring 95 to controller 125 for control and display of the fluid temperature. In particular, controller 125 receives the measured fluid temperature and controls thermal treatment devices 175 to thermally treat the fluid (e.g., heat and/or cool) to the desired temperature. Temperature controller 170 basically controls power to thermal treatment devices 175 based on a comparison of the temperature measured by temperature sensor 90 and the set point temperature entered by the user. For example, when the measured temperature exceeds the set point temperature, temperature controller 170 may disable or reduce power to thermal treatment devices 175 in the form of heating elements, and may enable or increase power to those devices in response to the measured fluid temperature falling below the set point temperature. Alternatively, the temperature controller may alternate heating and cooling modes of the thermal treatment devices in accordance with the comparison of the measured and set-point temperatures. Moreover, thermostat 190 may disable the thermal treatment device in response to a temperature measurement exceeding a temperature threshold as described above.

The temperature controller may further display the measured and/or set point temperatures or any other desired information on display 145. The information to display may be selected by a user via input devices 155. The controller may further actuate visual and/or audio indicators to inform an operator that the measured fluid temperature is beyond a set-point temperature or range as described above. In addition, processor 200 may produce a report including information received from temperature controller 170 and/or processor input devices as described above. The report may be produced by printer 210 or transmitted to another device via communications module 220 as described above. Upon completion of infusion, a temperature measurement or a medical procedure, sensor wiring 95 may be disengaged from the monitor device or controller, while the fitting (or IV line set including the fitting) is discarded.

Temperature sensing device 10 may alternatively be configured to releasably engage temperature sensor 90 as illustrated in FIG. 4. Specifically, temperature sensing device 10 is substantially similar to the temperature sensing device described above and includes fitting 20 with base portion 30 and projection 40. The projection extends transversely from an intermediate section of base portion 30, while base portion 30 includes open ends 50A, 50B and longitudinal channel or fluid conduit 60 configured to permit the flow of fluid through base portion 30 as described above. Open ends 50A, 50B may be removably secured to selected portions of IV line 70 (e.g., via Leur locks or other connectors 75) to form a reusable IV line set, or may be permanently secured to the IV line (e.g., by welding the ends of the fitting to portions of the IV line) to form a disposable IV line set.

A thermally conductive receptacle or cup 80 is disposed within projection 40 and extends partially within fluid channel 60 for contact with fluid flowing therein. Receptacle 80 is preferably formed from thermally conductive material (e.g., metals such as stainless steel, copper, aluminum etc.), and may be secured within the projection via any suitable securing techniques (e.g., friction fit, adhesives, etc.). Receptacle 80 includes dimensions sufficient to permit contact between the exterior surface of temperature sensor 90 and the interior bottom and/or side surfaces of the receptacle, where the receptacle and sensor are sized to enable the sensor to tightly fill the receptacle for efficient heat transfer from the fluid through the receptacle to the sensor. This enables an accurate temperature measurement of the fluid flowing within channel 60.

Referring to FIG. 5, receptacle 80 includes a generally cylindrical body 82 with a closed distal end 84 and an open proximal end 86 for receiving temperature sensor 90. The thickness of the receptacle walls and, in particular, the distal end 84, is sufficient to readily permit the conduction of heat therethrough. A flange 88 extends radially from the open proximal end of the receptacle to engage an interior surface of projection 40. The receptacle is secured within projection 40 and extends partially within base portion 30 to contact fluid flowing within base portion channel 60. Specifically, receptacle 80 extends into channel 60 for a distance sufficient to enable to temperature sensor 90 to provide an accurate temperature measurement, while not impeding fluid flow through the channel. By way of example, the receptacle should maximally extend approximately halfway into the channel, and preferably maximally extends approximately one quarter of the way into the channel. Temperature sensor 90 is substantially similar to the temperature sensor described above and may be secured within receptacle 80 via friction fit, a locking or securing mechanism, or any other securing techniques. Receptacle 80 includes dimensions sufficient to provide a fluid tight seal between projection 40 and base portion channel 60, thereby maintaining fluid within the channel. Sensor wiring 95 may connect temperature sensor 90 to monitor device 100 for display of the measured fluid temperature, or to controller 125 for control (e.g., of thermal treatment devices) and display of the fluid temperature as described above.

Operation of temperature sensing device 10 with receptacle 80 is described with reference to FIGS. 4-5. Initially, the operation of temperature sensing device 10 is similar to the operation of the temperature sensing device described above for FIG. 1. Specifically, temperature sensing device 10 is attached to IV line 70 by securing base portion open ends 50A, 50B to operator selected portions of the IV line. Sensor wiring 95 is connected to monitor device 100 for temperature display, or to controller 125 for temperature control and display as described above. Upon securing fitting 20 to IV line 70 in a fluid tight relationship, IV fluid is permitted to flow through the IV line and fitting. Distal end 84 of receptacle 80 contacts the fluid flowing within channel 60. Temperature sensor 90 is inserted into the receptacle with the distal end of the temperature sensor contacting the receptacle closed end. The fluid transfers heat to receptacle 80 and causes the receptacle to substantially attain the fluid temperature. Temperature sensor 90 directly measures the temperature of receptacle 80, thereby indirectly measuring the temperature of the fluid. The temperature sensor transmits the measured temperature information via sensor wiring 95 to monitor device 100 for display of fluid temperature, or to controller 125 for control and display of the fluid temperature as described above. The controller processor may generate and provide reports as described above.

Upon completion of infusion, a temperature measurement or a medical procedure, temperature sensor 90 is removed from receptacle 80 for additional use, while the fitting (or IV line set including the fitting) is discarded. Since the temperature sensor does not directly contact fluid flowing within the IV line, the system facilitates repeated use of the temperature sensor with additional IV lines without the need for sterilization.

Temperature sensing device 10 (FIG. 4) may further include a securing mechanism to releasably engage temperature sensor 90 to fitting 20 and properly position the temperature sensor within receptacle 80. For example, projection 40 and temperature sensor 90 may include mating threads to secure the temperature sensor to the fitting in substantially the same manner described above. Alternatively, the securing mechanism may enable a one-time use for the temperature sensor to maintain sterility as illustrated in FIGS. 6-7. Specifically, temperature sensor 90 may be secured to fitting 20 via a securing member or cap 600. The cap includes a generally cylindrical body 601; however, the cap may include an S-shaped body with ends tapering in thickness or other configurations to facilitate enhanced gripping. Cap 600 may be constructed of any suitable materials (e.g., plastic).

Cap 600 includes a channel 610 defined in the cap interior and extending from a cap proximal portion to a cap distal surface. Channel 610 is dimensioned to receive and retain fitting projection 40. Temperature sensor 90 is disposed within the cap channel and extends beyond the cap distal surface. Channel 610 is dimensioned to receive and retain fitting projection 40, while temperature sensor 90 includes transverse cross-sectional dimensions slightly less than those of receptacle 80 to enable insertion of the temperature sensor within the receptacle as described below. The cap proximal surface includes a support structure 620 disposed thereon to guide sensor wiring 95 and to provide structural support for cap 600. The sensor wiring is connected to temperature sensor 90 and extends through the cap proximal surface and support structure 620 to monitor device 100 or controller 125 as described above.

Projection 40 may further include tabs 545 disposed toward the projection proximal end and angularly spaced apart by approximately one-hundred eighty degrees. Cap channel 610 includes transverse cross-sectional dimensions slightly greater than those of projection 40, but less than those of the projection portions containing tabs 545. In order to accommodate the projection tab portions, channel 610 includes grooves 630 (FIG. 7) defined therein and angularly spaced apart by approximately one hundred eighty degrees. Grooves 630 extend from the cap distal surface toward the cap channel proximal end and include dimensions suitable to accommodate tabs 545. Recesses or notches 640 are defined at the proximal ends of the respective grooves and are dimensioned to receive and retain corresponding tabs 545. The transverse cross-sectional dimensions of tabs 545 are slightly greater than those of the channel with grooves 630, but less than the dimensions of the channel with recesses 640. Grooves 630 basically compress tabs 545 due to projection resiliency to receive those portions in a snug fashion and to guide the tabs toward recesses 640. The projection resiliency causes the projection to expand upon reaching recesses 640, thereby forcing tabs 545 in a locking engagement with those recesses. Locking of tabs 545 in the corresponding recesses 640 assures that temperature sensor 90 is seated properly in receptacle 80 and in contact with the receptacle. In addition, grooves 630 may taper in depth toward corresponding recesses 640 to assist in guiding tabs 545 through the grooves and into the recesses.

Tabs 545 are each configured to be fractured and removed from fitting 20. This prevents the fitting from being re-used for temperature measurement, thereby maintaining fluid sterility. The tabs may be removed from the fitting by rotating cap 600 with respect to projection 40 when the tabs are disposed within recesses 640. The recesses inhibit tab motion, thereby enabling the rotational force applied to the cap to fracture and remove the tabs from the fitting. Recesses 640 may further be elongated transversely on the cap interior surface to permit initial free rotational movement of cap 600 and enhance application of rotational force to the cap for fracturing the tabs.

Operation of temperature sensing device 10 (FIG. 4) with the securing mechanism is described with reference to FIGS. 6-7. Initially, temperature sensing device 10 is connected to an operator selected portion of IV line 70 in substantially the same manner described above. Basically, first and second open ends 50A, 50B are attached to respective portions of IV line 70. Upon securing fitting 20 to IV line 70, fluid is permitted to flow through the IV line and the fitting. The distal end of receptacle 80 contacts the fluid flowing through fitting channel 60. Temperature sensor 90 is inserted into the receptacle with the distal end of the temperature sensor contacting the receptacle closed end. Securing cap 600 is disposed over projection 40 with temperature sensor 90 positioned within projection 40 and grooves 630 aligned with tabs 545. Cap 600 is forced distally onto the projection to allow tabs 545 to travel proximally through grooves 630 and become secured within the recesses 640, while temperature sensor 90 is inserted into receptacle 80. Upon securing tabs 545 within the recesses, cap 600 is effectively locked on fitting 20 with temperature sensor 90 contacting the interior surface of receptacle 80.

The fluid flowing within fitting channel 60 transfers heat to receptacle 80 to cause the receptacle to substantially attain the fluid temperature. Temperature sensor 90 directly measures the temperature of the receptacle, thereby indirectly measuring the temperature of the fluid. The temperature sensor may transmit the measured temperature information via sensor wiring 95 to the monitor device for display, or to controller 125 for control (e.g., of thermal treatment devices) and display of the fluid temperature as described above. The controller processor may provide reports including information received from the temperature controller and/or processor input devices as described above.

Once the infusion, temperature measurement or medical procedure is completed, the locking engagement between cap 600 and fitting 20 may be released by rotating the cap relative to projection 40. This causes tabs 545 to fracture and be removed from the projection, thereby disengaging the cap and temperature sensor 90 from fitting 20. Once cap 600 is removed, fitting 20 and/or the IV line set is discarded. Thus, the temperature sensing device with the securing mechanism facilitates temperature measurement without direct contact of fluid and employs a temporary locking arrangement between the temperature sensor and the fitting, thereby allowing reuse of the temperature sensor and securing cap with additional fittings without the need for sterilization. Further, the fitting is limited to a single use for temperature measurement to prevent contamination of sterile fluid. In addition, the tabs may notify an operator of fitting use. Basically, since the securing cap removes the projection tabs after use, the absence of those tabs on the fitting indicates that the fitting has been previously used and may compromise sterile conditions when used for another application.

Figure 8A:
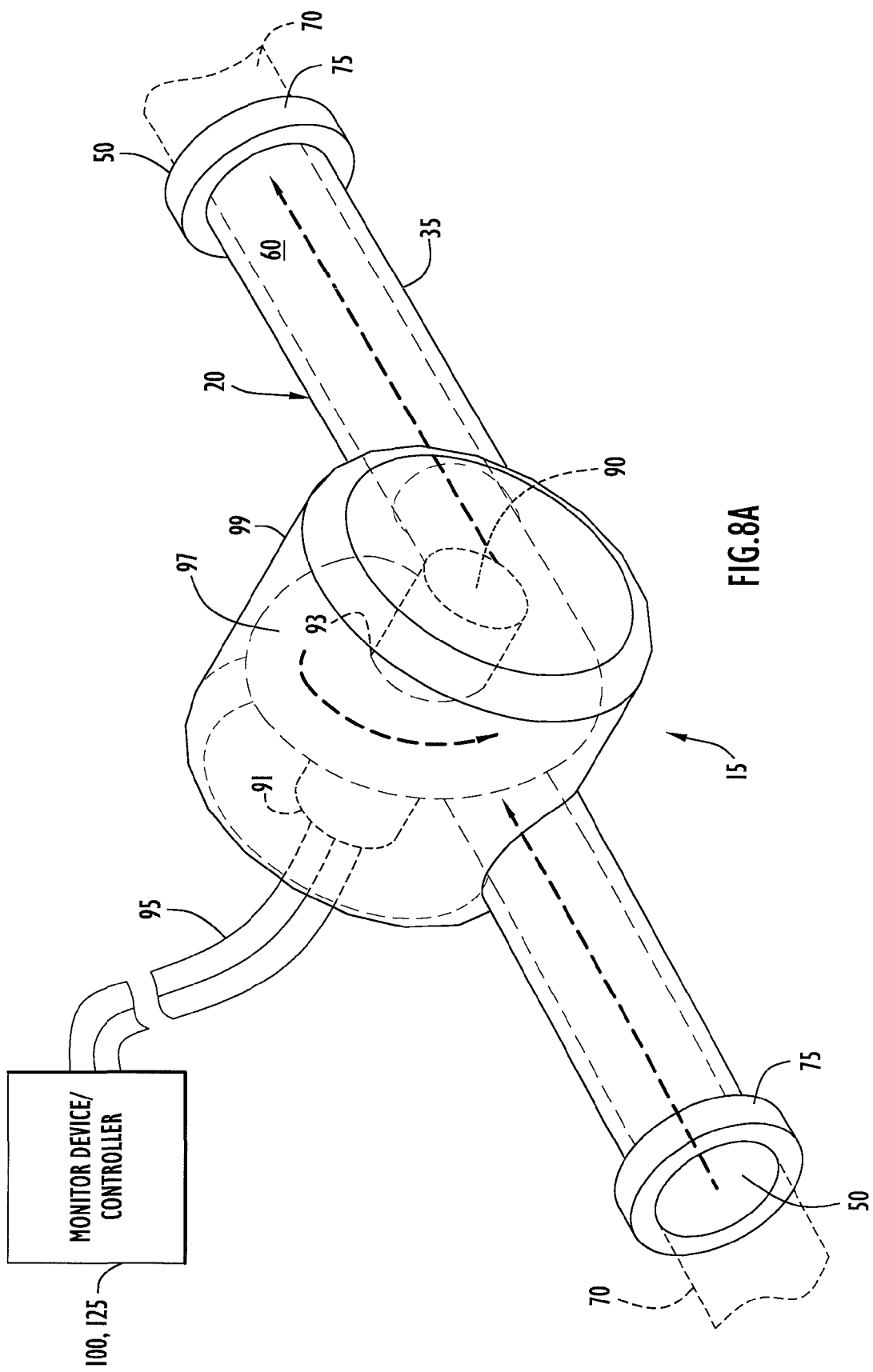
FIGS. 8A-8C are perspective views of a temperature sensing device in the form of a line fitting including a looping fluid flow path surrounding a temperature sensor according to embodiments of the present invention.
Figure 8B:
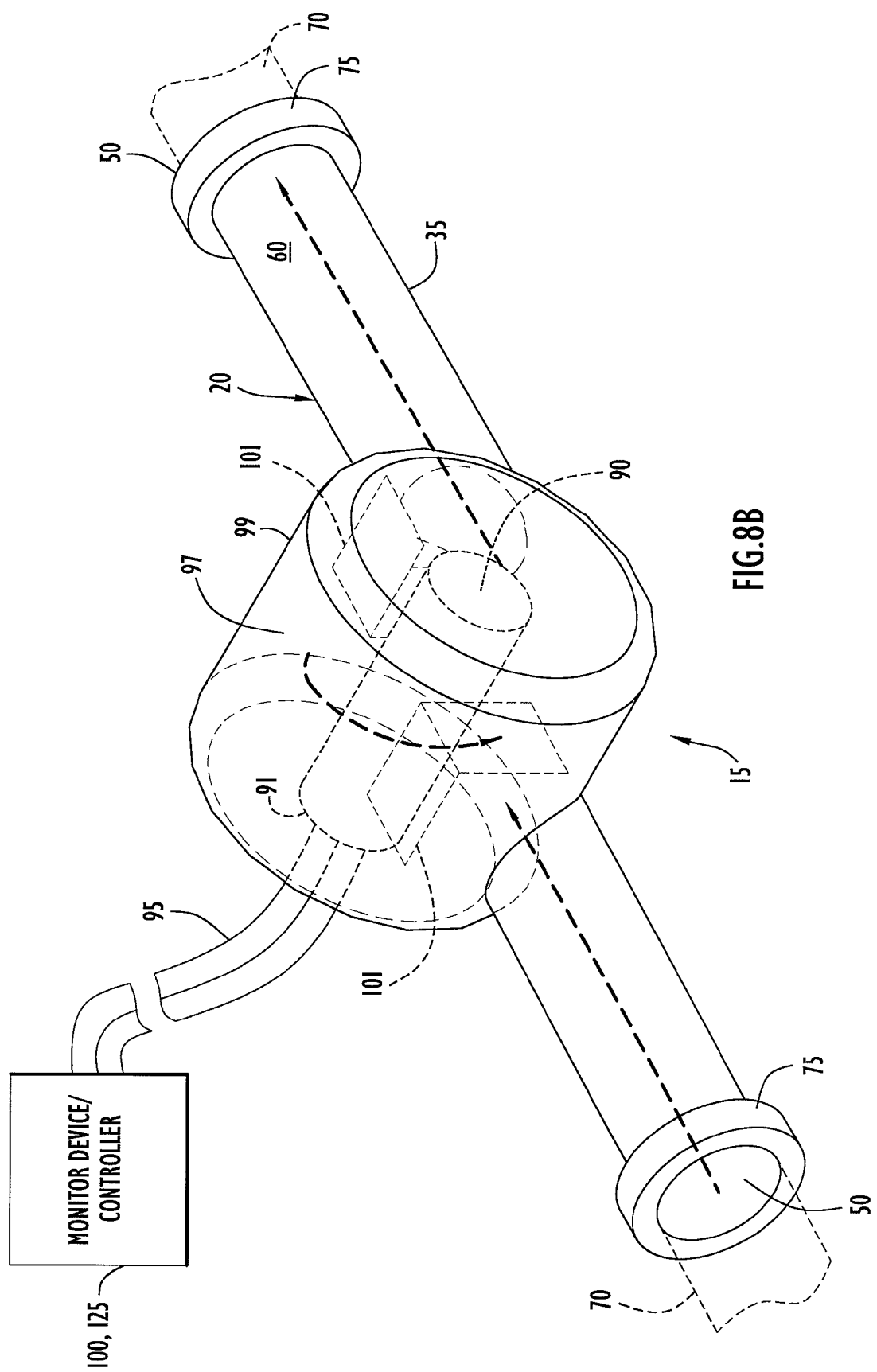

In order to expose a larger surface area of temperature sensor 90 to the IV fluid for an enhanced temperature measurement, the temperature sensing device may alternatively include a looped configuration as illustrated in FIGS. 8A-8B. Initially, temperature sensing device 15 is similar to temperature sensing device 10 described above for FIG. 1 and includes a fitting 20 including a base portion 35 with open ends 50A, 50B and a fluid channel 60 defined within the base portion to permit fluid flow through the fitting. Open ends 50A, 50B may be removably secured to selected portions of IV line 70 via Leur locks or other connectors 75, or may be permanently secured to the IV line (e.g., by welding the ends of the fitting to portions of the IV line) to form a disposable IV line set in substantially the same manner described above.

Fitting 20 is substantially similar to fitting 20 of temperature sensing device 10 (FIG. 1) described above, and includes base portion 35 with a looped configuration. In particular, base portion 35 forms a substantially spiral type loop 97 between open ends 50A, 50B to define a looped path for fluid flowing within the fitting. Loop 97 is housed within a substantially cylindrical housing portion 99 with a substantially central transverse aperture 91 defined within a housing portion side wall. The loop similarly includes a substantially central transverse aperture 93, where apertures 91, 93 are aligned and dimensioned to receive temperature sensor 90 therethrough. In other words, loop 97 is configured to wrap around the temperature sensor within housing portion 99. The temperature sensor is substantially similar to the temperature sensor described above. Alternatively, housing portion 99 may include a hollow interior and enable fluid to surround the temperature sensor within the housing portion (e.g., without a preconfigured base portion), or the housing portion may include a series of dividers 101 (FIG. 8B) defining a looped fluid flow path about the temperature sensor within the housing portion. However, any suitable looping or other configuration may be employed to surround the temperature sensor with the fluid.

Temperature sensor 90 is integrated into the base portion, where the temperature sensor external surface serves as a portion of the interior surface for loop 97, thereby enabling the temperature sensor to directly contact the fluid flowing within the fitting. For example, temperature sensor 90 may be molded directly into fitting 20 and serve as the interior surfaces for portions of the loop wrapping around the temperature sensor. This looped configuration provides an increased surface area of the temperature sensor for contacting the fluid flowing through fitting 20 without restricting fluid flow, thereby providing a temperature measurement with enhanced accuracy. Temperature sensing device 15 may include any quantity (e.g., one or more) of loops 97 to increase the surface area of the temperature sensor contacting fluid and accuracy of the resulting temperature measurement. Sensor wiring 95 may transmit the measured temperature information to monitor device 100 for display of the measured temperature, or to controller 125 for display and control (e.g., of thermal treatment devices) of the fluid temperature in substantially the same manner described above.

Figure 8C:
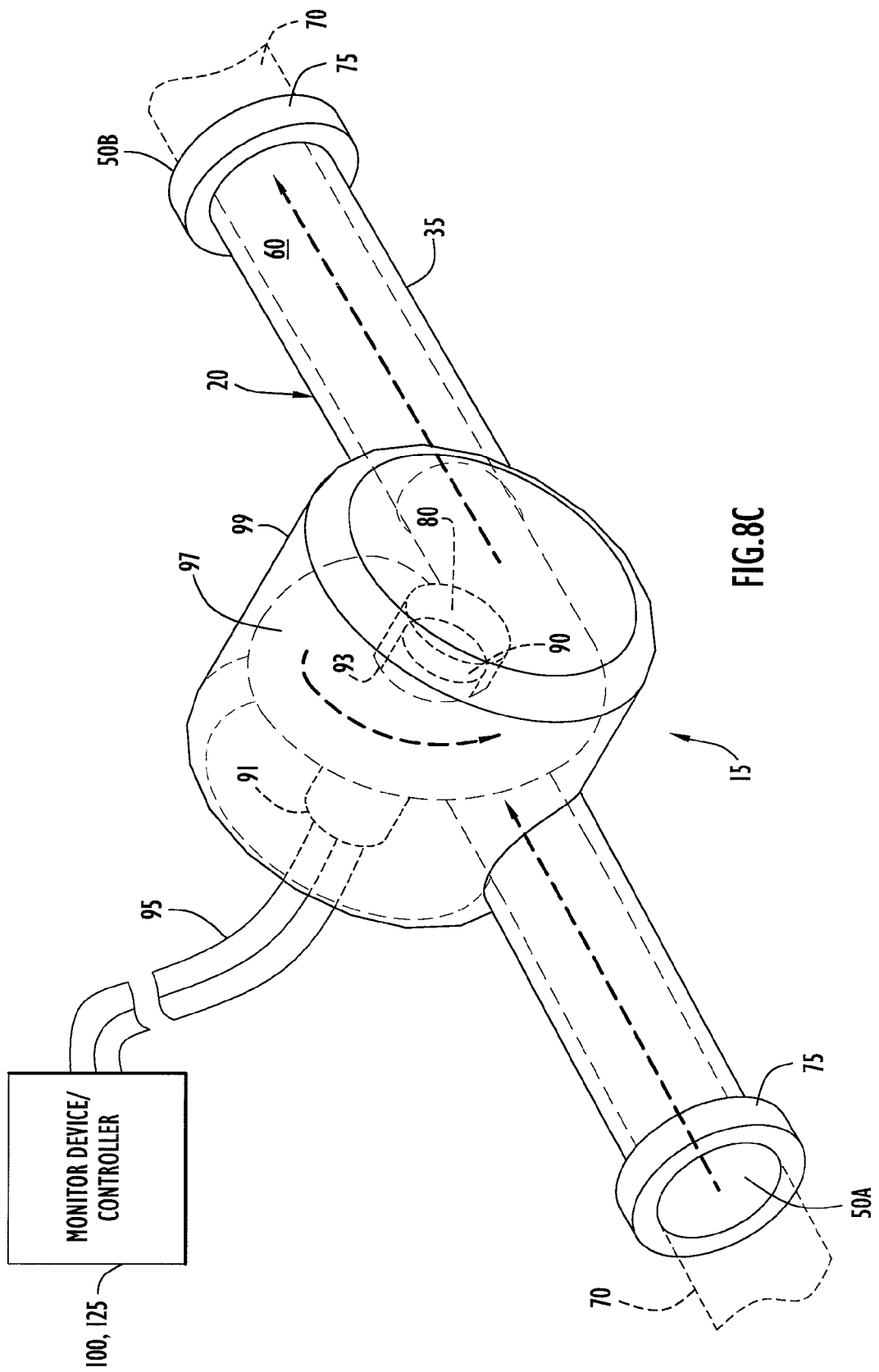

Temperature sensing device 15 may alternatively employ receptacle 80 as illustrated in FIG. 8C. Specifically, temperature sensing device 15 may be substantially similar to the temperature sensing device described above for FIG. 8A, and includes receptacle 80 disposed within transverse apertures 91, 93 of the housing portion and loop, respectively. The receptacle is substantially similar to the receptacle described above and receives temperature sensor 90 to measure temperature of fluid. The temperature sensor is substantially similar to the temperature sensor described above. In this case, apertures 91, 93 are aligned and dimensioned to receive receptacle 80 therethrough. In other words, loop 97 is configured to wrap around the receptacle. Receptacle 80 is integrated into the base portion, where the receptacle external surface serves as a portion of the interior surface for loop 97, thereby enabling the receptacle to directly contact the fluid flowing within the fitting. For example, the receptacle may be molded directly into fitting 20 and serve as the interior surfaces for portions of the loop wrapping around the receptacle. This looped configuration provides an increased surface area of the receptacle for contacting the fluid flowing through fitting 20 without restricting fluid flow, thereby providing a temperature measurement by temperature sensor 90 with enhanced accuracy. Temperature sensing device 15 may include any quantity (e.g., one or more) of loops 97 to increase the surface area of the receptacle contacting fluid and accuracy of the resulting temperature measurement, and may further include any of the looping or other configurations described above (e.g., FIG. 8B, etc.).

Temperature sensor 90 is inserted within receptacle 80, preferably in direct contact with the receptacle. The temperature sensor may be secured in position in substantially the same manners described above (e.g., friction fit, etc.). Further, temperature sensing device 15 may include a projection substantially similar to projection 40 described above and extending from aperture 93 to secure the temperature sensor within the receptacle. The projection may include a threaded arrangement or the securing arrangement described above for FIGS. 6-7. The fluid flowing within fitting channel 60 transfers heat to receptacle 80 and causes the receptacle to substantially attain the fluid temperature. Temperature sensor 90 directly measures the temperature of the receptacle, thereby indirectly measuring the temperature of the fluid. The temperature sensor may transmit the measured temperature information via sensor wiring 95 to the monitor device for display, or to controller 125 for control (e.g., of thermal treatment devices) and display of the fluid temperature as described above.

Operation of temperature sensing device 15 is described with reference to FIGS. 8A-8C. Initially, temperature sensing device 15 is connected to an operator selected portion of IV line 70 in substantially the same manner described above. Basically, first and second open ends 50A, 50B are attached to respective portions of IV line 70. Upon securing fitting 20 to IV line 70, fluid is permitted to flow through the IV line and the fitting. The temperature sensor (FIGS. 8A-8B) contacts the fluid flowing through the looped path of the fitting as described above to measure the fluid temperature.

Alternatively, temperature sensor 90 is inserted into receptacle 80 (FIG. 8C) with the distal end of the temperature sensor contacting the receptacle closed end. The receptacle contacts the fluid flowing through loop 97 of fitting channel 60 as described above. The fluid flowing within fitting channel 60 transfers heat to receptacle 80 and causes the receptacle to substantially attain the fluid temperature. Temperature sensor 90 directly measures the temperature of the receptacle, thereby indirectly measuring the temperature of the fluid.

The temperature sensor may transmit the measured temperature information via sensor wiring 95 to the monitor device for display, or to controller 125 for control and display of the fluid temperature as described above. The controller processor may provide reports including information received from the temperature controller and/or processor input devices as described above.

Once the infusion, temperature measurement or medical procedure is completed, sensor wiring 95 may be disengaged from the monitor device or controller, while the fitting (or the IV line set including the fitting) is discarded. In the case when receptacle 80 is employed, the temperature sensor is removed from the receptacle for additional use, while the fitting (or the IV line set including the fitting) is discarded.

Temperature sensing device 10 may further include a valve operable to selectively control the flow of fluid through fitting 20 as illustrated in FIGS. 9A-9B. This allows medical personnel to interrupt the fluid flow and check the temperature of fluid within the IV line prior to administration to a patient. Once the fluid temperature is verified, the valve is opened to enable fluid to flow to the patient. The valve may further include a lock to prevent interruption of the fluid flow after the flow has been enabled. In particular, temperature sensing device 10 is substantially similar to the temperature sensing device described above for FIG. 4 and includes fitting 20 including base portion 30 and projection 40 extending transversely from an intermediate section of the base portion. Fitting 20 further includes a flow controller or valve 300 extending transversely from an intermediate section of base portion 30 at a position downstream from projection 40. Base portion 30 is substantially cylindrical with open ends 50A, 50B and longitudinal channel or fluid conduit 60 defined therethrough as described above. Projection 40 serves to engage and secure receptacle 80 within fitting 20 to enable the receptacle to contact fluid flowing though base portion channel 60 for a temperature measurement by temperature sensor 90 as described above. The temperature sensor is substantially similar to the temperature sensor described above. Sensor wiring 95 may connect temperature sensor 90 to monitor device 100 for display of the measured fluid temperature, or to controller 125 for control (e.g., of thermal treatment devices) and display of the fluid temperature as described above.

Open ends 50A, 50B of base portion 30 may be removably secured to selected portions of IV line 70 via Luer locks or other connectors 75 to form a reusable IV line set, or may be permanently secured to IV line 70 (e.g., by welding the ends of the fitting to portions of the IV line) to form a disposable IV line set.

Flow controller 300 controls the flow of fluid through fitting 20 and may be a plunger type valve that selectively permits or prevents the flow of fluid through fitting 20. In particular, flow controller 300 includes a housing 310 and a piston 320. The housing is transversely disposed through an intermediate section of base portion 30 at a location downstream from projection 40. Housing 310 includes a substantially cylindrical passage 330 extending from a housing open proximal end to a housing closed distal end. Passage 330 includes dimensions sufficient to slidably receive piston 320 therein. Openings 340 are defined within opposing sections of a housing intermediate portion and aligned with longitudinal channel 60 of base portion 30. The dimensions of openings 340 are substantially similar to the dimensions of longitudinal channel 60 to permit flow of fluid through that channel (e.g., housing 310 does not impede the flow of fluid through fitting 20). Housing 310 may be secured to fitting 20 in any suitable manner. By way of example, housing 310 may be molded into fitting 20.

Piston 320 includes a distal core member 350 and a proximal gripping member 360. A connector element or extension member 365 extends axially from a substantially central location on the distal end of gripping member 360 to a substantially central location on the proximal end of core member 350. Connector element 365 is substantially cylindrical and includes a diameter slightly less than that of both core member 350 and gripping member 360. The gripping member is configured to permit a user to grasp the member in order to control the fluid flow. Gripping member 360 extends proximally from the proximal end of connector element 365. The gripping member is substantially cylindrical and includes a diameter greater than that of housing passage 330 to enable the housing distal end to form a stop and prevent the axial insertion of core member 350 into housing 310 beyond gripping member 360.

Core member 350 extends distally from the distal end of connector element 365 and is coaxially positioned within housing 310. The core member is in the form of a substantially cylindrical rod including closed distal and proximal ends. Core member 350 is contoured for compatibility with the interior surface of housing 310 and includes a diameter that provides a sliding and fluid tight engagement between housing 310 and core member 350. In addition, core member 350 may include dimensions sufficient to form a fluid tight seal along longitudinal channel 60 of base portion 30 (e.g., the core member prevents fluid from flowing along the longitudinal channel when positioned therein). Core member 350 may be partially or fully disposed within housing 310. An aperture 370 is defined within an intermediate portion of core member 350 for selective alignment with housing openings 340. This alignment opens the flow controller (e.g., permits fluid to flow through fitting 20) and may be accomplished by inserting the core member into housing 310 (FIG. 9B).

Flow controller 300 may further include a locking mechanism to secure piston 320 in a position within housing 310 to open the flow controller (e.g., permit fluid to flow though fitting 20). In particular, a rib or protrusion 380 may be disposed on the periphery of the core member distal end, while a recess 385 corresponding to rib 380 may be disposed proximate the housing closed distal end. Recess 385 is configured to engage and permanently secure rib 380 therein in response to the core member being forced toward the housing distal end. With this configuration, the core member is locked with the flow controller in an open state, where flow controller 300 may be configured as a one-time use valve that prevents interruption of the fluid flow once the flow controller has been opened. Alternatively, flow controller 300 may be configured to selectively open and close. Temperature sensing device 10 with the flow controller may alternatively be implemented with temperature sensor 90 directly contacting fluid (without receptacle 80) in a manner similar to that described above for FIG. 1.

Operation of temperature sensing device 10 including a piston-type flow controller or valve 300 is described with reference to FIGS. 9A-9B. Temperature sensing device 10 is attached to IV line 70 by securing base portion open ends 50A,B to operator selected portions of the IV line as described above. Flow controller 300 is set to a closed configuration with core member 350 in a proximal position within housing 310 and aperture 370 of core member 350 not aligned with housing openings 340 (FIG. 9A). Upon securing fitting 20 to IV line 70, IV fluid is permitted to flow through the IV line and fitting. Flow controller 300 impedes further flow of the fluid through fitting 20, while temperature sensor 90 measures the temperature of the fluid as described above. The temperature information may be transmitted to the monitor device for display, or to controller 125 for control and display of the fluid temperature.

When the fluid reaches the desired temperature, flow controller 300 is manually set to the opened configuration (FIG. 9B). Specifically, a force is applied to gripping member 360 (e.g., as indicated by arrow F in FIG. 9B)) to axially urge or slide core member 350 distally within housing 310 until the core member distal end engages the housing closed distal end. Rib 380 of the core member engages recess 385 of the housing, thereby locking the flow controller in an opened position. Once fully inserted, core member aperture 370 and housing opening 340 are substantially aligned and fluid is free to flow through longitudinal channel 60 and IV line 70 toward a patient. Upon completion of infusion, an IV fluid temperature measurement or medical procedure, temperature sensor 90 is removed from receptacle 80 for additional use, while the fitting (and/or IV line set including the fitting) is discarded.

Figure 9C:
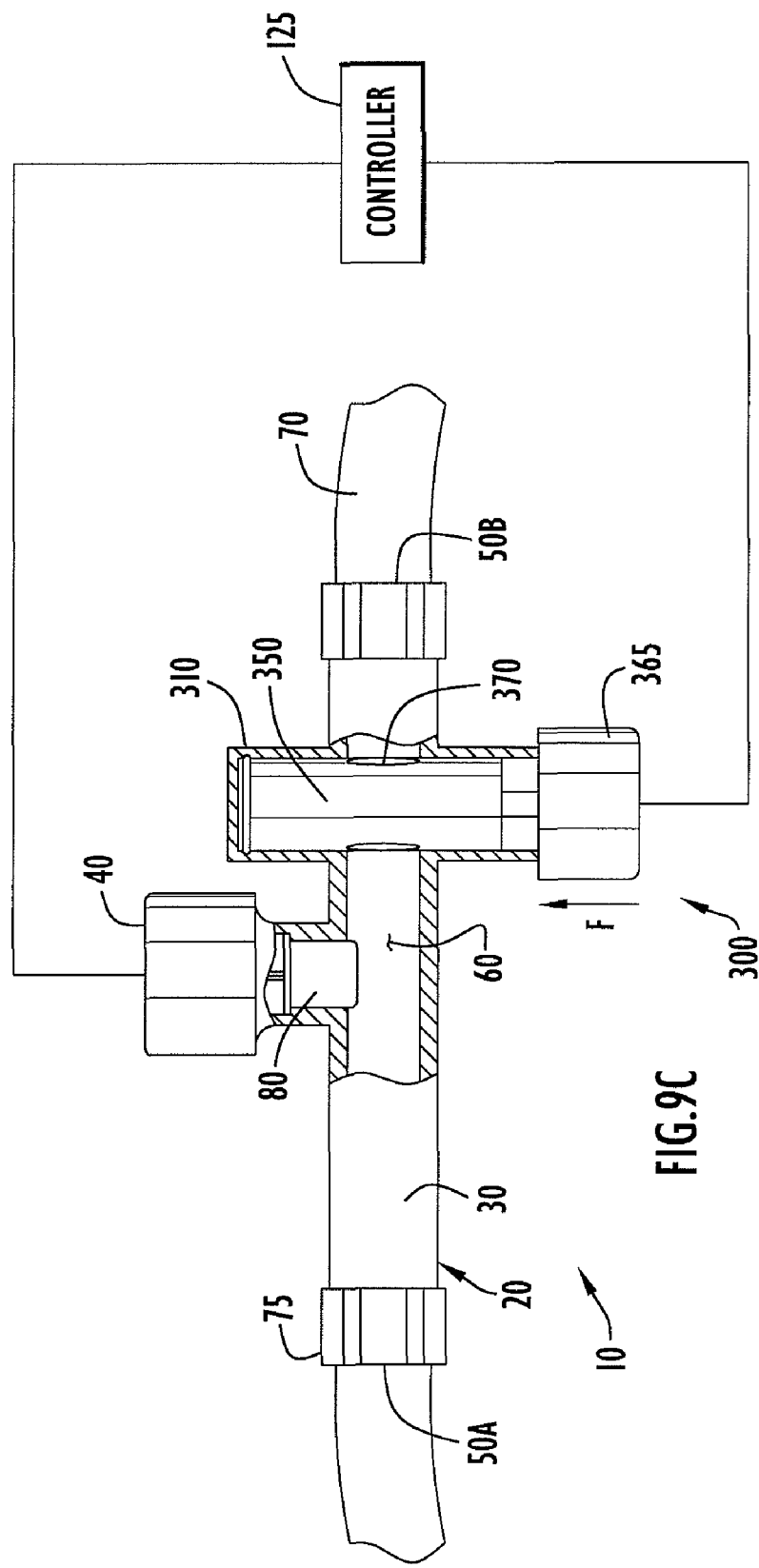

Flow controller 300 of temperature sensing device 10 may further be controlled by controller 125 based on a temperature measurement as illustrated in FIG. 9C. This ensures that the fluid within the IV line has attained the desired temperature prior to administration to a patient. In particular, temperature sensing device 10 is substantially similar to the temperature sensing device described above for FIGS. 9A-9B and includes fitting 20 including base portion 30 and projection 40 extending transversely from an intermediate section of the base portion. Projection 40 serves to engage and secure receptacle 80 within fitting 20 to enable the receptacle to contact fluid flowing though base portion channel 60 for a temperature measurement by temperature sensor 90 as described above. The temperature sensor is substantially similar to the temperature sensor described above. Sensor wiring 95 connects temperature sensor 90 to controller 125 for control (e.g., of thermal treatment devices, flow controller, etc.) and display of the fluid temperature as described below.

Fitting 20 further includes flow controller or valve 300 extending transversely from an intermediate section of base portion 30 at a position downstream from projection 40 as described above. The flow controller includes housing 310 and piston 320 with distal core member 350 as described above. A solenoid or actuator 367 is attached to the proximal end of housing 310 and coupled to controller 125. The solenoid may be integral with the temperature sensing device, or may be releasably secured to housing 310 (e.g., via a threaded, friction fit, or other arrangement, etc.) to enable the solenoid to be reused with other fittings without sterilization and compromising sterility. The solenoid may be implemented by any conventional or other actuator. Connector element or extension member 365 extends axially from a substantially central location on the distal end of solenoid 367 to a substantially central location on the proximal end of core member 350 to enable the solenoid to manipulate the core member.

Controller 125 receives a temperature measurement from temperature sensor 90 as described above. When the measured temperature is within a desired range of the set-point temperature for the fluid, controller 125 (e.g., via temperature controller 170 (FIG. 3)) actuates solenoid 367 to urge core member 350 distally within housing 310 to open the flow controller and permit fluid flow. In particular, the core member is forced distally (e.g., as indicated by arrow F in FIG. 9C) within the housing by the solenoid to align core member aperture 370 with housing apertures 340 to open the valve and permit fluid flow in substantially the same manner described above. The controller may further actuate the solenoid to force the core member proximally within the housing to close the flow controller and interrupt the flow. This may occur when the controller determines the fluid temperature measurement to be excessive or beyond a desired range of the set-point temperature. The desired ranges may be entered by a user into controller 125. Temperature sensing device 10 with the controlled flow controller may alternatively be implemented with temperature sensor 90 directly contacting fluid (without receptacle 80) in a manner similar to that described above for FIG. 1.

Operation of temperature sensing device 10 including the controlled piston-type flow controller or valve is described with reference to FIG. 9C. Temperature sensing device 10 is attached to IV line 70 by securing base portion open ends 50A, 50B to operator selected portions of the IV line as described above. Flow controller 300 is coupled to controller 125 and typically initially resides in a closed configuration with core member 350 in a proximal position within housing 310 and aperture 370 of core member 350 not aligned with housing openings 340. Upon securing fitting 20 to IV line 70, IV fluid is permitted to flow through the IV line and fitting. Flow controller 300 impedes further flow of the fluid through fitting 20, while temperature sensor 90 measures the temperature of the fluid as described above. The temperature information is transmitted to controller 125 for control and display of the fluid temperature as described above.

When the fluid reaches the desired temperature, controller 125 actuates solenoid 367 to set the flow controller in the opened configuration. Specifically, solenoid 367 applies a force (e.g., as indicated by arrow F in FIG. 9C)) to axially urge or slide core member 350 distally within housing 310 until the core member distal end engages the housing closed distal end. Once fully inserted, core member aperture 370 and housing openings 340 are substantially aligned and fluid is free to flow through longitudinal channel 60 and IV line 70 toward a patient. Controller 125 may further actuate solenoid 367 to force the core member proximally within housing 310 and close the flow controller when the measured fluid temperature is beyond a desired temperature range. Upon completion of infusion, an IV fluid temperature measurement or medical procedure, temperature sensor 90 and/or solenoid 367 may be disconnected from the fitting for additional use, where the fitting (or IV line set including the fitting) may be discarded.

An embodiment of temperature sensing device 10 with an alternative flow controller is illustrated in FIGS. 10A-10C. Temperature sensing device 10 is substantially similar to the temperature sensing device described above for FIG. 4, and includes a flow controller 400 including a twist or ball type valve device operable to rotate about a device longitudinal axis. In particular, temperature sensing device 10 includes fitting 20 including base portion 30 and projection 40 extending transversely from an intermediate section of the base portion. Fitting 20 further includes flow controller or valve 400 extending transversely from an intermediate section of base portion 30 at a position downstream from projection 40. Base portion 30 is substantially cylindrical with open ends 50A, 50B and longitudinal channel or fluid conduit 60 defined therethrough as described above. Projection 40 serves to engage and secure receptacle 80 within fitting 20 to enable the receptacle to contact fluid flowing though base portion channel 60 for a temperature measurement by temperature sensor 90 as described above. The temperature sensor is substantially similar to the temperature sensor described above. Sensor wiring 95 may connect temperature sensor 90 to monitor device 100 for display of the measured fluid temperature, or to controller 125 for control (e.g., of thermal treatment devices) and display of the fluid temperature as described above.

Open ends 50A, 50B of base portion 30 may be removably secured to selected portions of IV line 70 via Luer locks or other connectors 75 to form a reusable IV line set, or may be permanently secured to IV line 70 (e.g., by welding the ends of the fitting to portions of the IV line) to form a disposable IV line set.

Flow controller 400 controls the flow of fluid through fitting 20 and may be a twist or ball type valve that selectively permits or prevents the flow of fluid through fitting 20. The flow controller includes a housing 410 and a rotatable valve member 420. The housing extends transversely from an intermediate section of base portion 30 at a location downstream from projection 40. Housing 410 serves to engage and secure valve member 420 within the fitting in a fluid right relationship. The housing is generally cylindrical and includes open ends that facilitate access to base portion channel 60. Housing 410 may be secured to fitting 20 utilizing any manner suitable to provide a fluid tight relationship and/or may be formed integral with the fitting.

Valve member 420 includes a core member 430 and a proximal cap or gripping member 440. The core member is substantially cylindrical with a substantially spherical distal portion 435. The gripping member is substantially cylindrical and includes a diameter greater than that of housing 410. Gripping member 440 includes closed proximal and distal ends, and an exterior peripheral wall that extends distally to form an annular gap 450 between that gripping member wall and housing 410. With this configuration, a user can rotate valve member 420 to manipulate flow controller 400.

A connector element or extension member 460 extends axially from a substantially central location on the gripping member distal end to a substantially central location on the core member proximal end. Connector element 460 is substantially cylindrical and includes a diameter slightly less than that of both core member 430 and gripping member 440. The core member extends distally from a connector element distal end with distal portion 435 disposed proximate longitudinal channel 60. Core member 430 is preferably coaxially positioned within housing 410 and may be contoured for compatibility with the interior surface of the housing. The core member includes a diameter operable to provide a fluid tight seal between the housing interior surface and core member 430 and to enable the core member to rotate within the housing. In addition, the dimensions of core member distal portion 435 are typically greater than the dimensions of longitudinal channel 60 of base portion 30 to form a fluid tight seal along longitudinal channel 60 when core member 430 is inserted into base portion 30. A securing plate or swivel 437 is attached to the distal end of core member distal portion 435, preferably through base portion 30. The plate is generally circular in the form of a disk and secures the core member in position within housing 410. The core member is rotatably connected to plate 437 and rotates relative to the housing to open and close the flow controller as described below.

An aperture 470 is transversely defined within distal portion 435 of core member 430 to enable alignment with longitudinal channel 60. Since core member 430 is configured to rotate within housing 410 as described above, aperture 470 may be selectively aligned with longitudinal channel 60 to manipulate the flow of fluid through fitting 20. Specifically, core member 430 may be rotated to align aperture 470 with longitudinal channel 60 to open the flow controller and permit fluid to flow through fitting 20 and IV line 70 to the patient. Conversely, the core member may be rotated to misalign aperture 470 with longitudinal channel 60 to close the flow controller and prevent the flow of fluid through fitting 20 and IV line 70. The degree of angular rotation required to align/misalign aperture 470 is preferably ninety degrees, but may be any suitable angular rotation to control fluid flow (e.g., any degree to provide full, partial and/or no fluid flow).

Flow controller 400 may further include a securing mechanism to lock the flow controller in an open position with core member aperture 470 aligned with channel 60 (FIG. 10C). Specifically, the external surface of the proximal end of housing 410 includes a plurality of shoulders or ramps 445. Housing shoulders 445 are each generally right triangular with a longer dimensioned edge extending along the housing external surface, a shorter dimensioned edge extending transversely from the housing external surface into annular gap 450 toward the gripping member, and a hypotenuse edge extending between these edges. The shoulders are angularly spaced apart on the housing external surface by approximately one-hundred eighty degrees.

The distal end of the gripping member includes a plurality of channels or grooves 449 defined therein. The channels extend along the gripping member distal end and each include an end tapered in width. A shoulder or ramp 447 is disposed within each groove toward the tapered end, and each shoulder 447 includes dimensions less than those of shoulders 445. The gripping member shoulders are each generally right triangular with a longer dimensioned curved edge extending along the gripping member or groove internal surface, a shorter dimensioned edge extending transversely from the gripping member or groove internal surface toward the housing, and a curved hypotenuse edge extending between these edges. The grooves (and shoulders) are angularly spaced apart on the gripping member surface by approximately one-hundred eighty degrees. The shorter dimensioned edges of shoulders 445, 447 are oriented and include dimensions sufficient to enable these edges to abut each other within grooves 449 as described below.

When the flow controller is in a closed position, shoulders 445 are generally disposed within corresponding grooves 449 and separated from shoulders 447 by a sufficient distance to enable rotation of the gripping member relative to the housing. However, in response to rotation of the gripping member to open flow controller 400 as described above, shoulders 445 traverse corresponding grooves 449 toward gripping member shoulders 447. The hypotenuse edges of shoulders 445, 447 contact and traverse each other to enable shoulders 445 to be positioned within the tapered ends of the corresponding grooves with the shorter dimensioned edges of shoulders 445, 447 abutting each other. The abutting edges of the shoulders serve as a stop and prevent rotation of the gripping member in a first direction. Similarly, the tapered ends of grooves 449 serve as a stop for housing shoulders 447, thereby preventing rotation of the gripping member in the other direction. Thus, the gripping and core members are effectively locked in position to maintain the flow controller in an open state. The flow controller may alternatively include any other suitable locking mechanism to releasably or permanently lock the gripping member and/or core member to maintain the flow controller in an open position. Temperature sensing device 10 with flow controller 400 may alternatively be implemented with temperature sensor 90 directly contacting fluid (without receptacle 80) in a manner similar to that described above for FIG. 1.

Operation of temperature sensing device 10 with flow controller 400 is described with reference to FIGS. 10A-10C. Temperature sensing device 10 including flow controller 400 is attached to IV line 70 by securing base portion open ends 50A, 50B to operator selected portions of the IV line. Flow controller 400 is initially set to the closed configuration (FIG. 10A) with aperture 470 not aligned with base portion channel 60 to prevent fluid flow through the fitting. Upon securing fitting 20 to IV line 70 in a fluid tight relationship, IV fluid is permitted to flow through the IV line, but is not allowed to exit the fitting due to the core member closed position. Temperature sensor 90 is axially inserted through projection 40 and into receptacle 80 to enable the temperature sensor to contact the interior surfaces of the receptacle. The fluid contacts and transfers heat to the exterior surface of receptacle 80 enabling the temperature sensor to indirectly measure the fluid temperature. Temperature sensor 90 transmits the measured temperature information via sensor wiring 95 to monitor device 100 for display, or to controller 125 for display and control of fluid temperature as described above. The controller processor may produce reports with information from the temperature controller and/or processor input devices as described above.

When the fluid reaches the desired temperature, flow controller 400 is set to the open position (FIG. 10B). Specifically, gripping member 440 is manipulated to rotate core member 430 (e.g., as indicated by arrow R in FIG. 10B) and align aperture 470 with base portion channel 60. When the locking mechanism is employed (FIG. 10C), housing shoulders 445 traverse corresponding gripping member grooves 449 in response to rotation of the gripping member. Shoulders 445 traverse gripping member shoulders 447 and become trapped within grooves 449 between the corresponding groove tapered end and a gripping member shoulder as described above. Thus, the gripping member is locked into position to maintain the flow controller in an open state.

Once flow controller 400 is set to the open position, fluid flows along channel 60 and through IV line 70 to a patient. Upon completion of infusion, an IV fluid temperature measurement or medical procedure, temperature sensor 90 is removed from receptacle 80 for additional use, while the fitting (or IV line set including the fitting) is discarded.

Figure 10D:
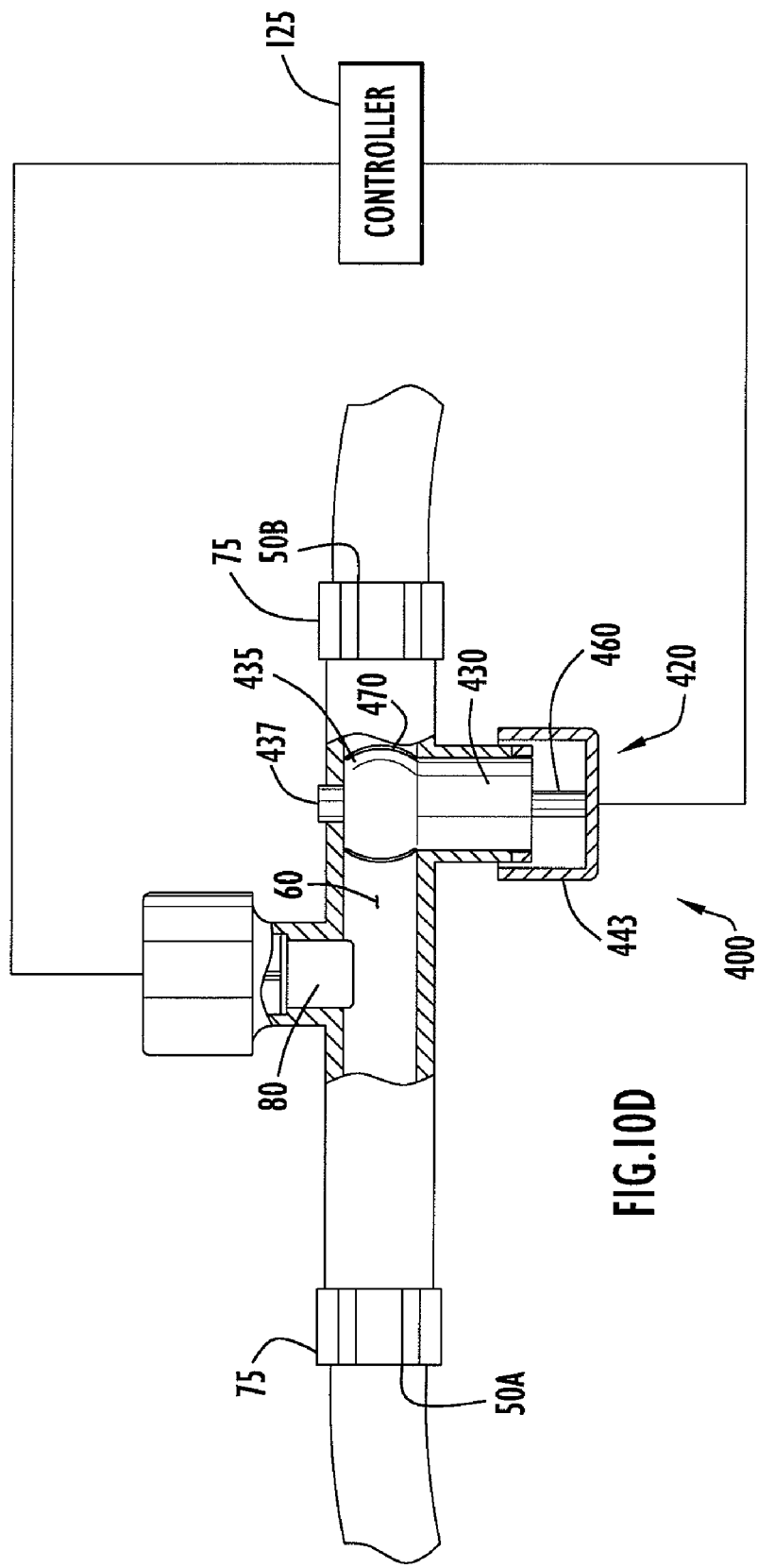

Flow controller 400 of temperature sensing device 10 may further be controlled by controller 125 based on a temperature measurement as illustrated in FIG. 10D. This ensures that the fluid within the IV line has attained the desired temperature prior to administration to a patient. In particular, temperature sensing device 10 is substantially similar to the temperature sensing device described above for FIGS. 10A-10C and includes fitting 20 including base portion 30 and projection 40 extending transversely from an intermediate section of the base portion. Projection 40 serves to engage and secure receptacle 80 within fitting 20 to enable the receptacle to contact fluid flowing though base portion channel 60 for a temperature measurement by temperature sensor 90 as described above. The temperature sensor is substantially similar to the temperature sensor described above. Sensor wiring 95 connects temperature sensor 90 to controller 125 for control (e.g., of thermal treatment devices, flow controller, etc.) and display of the fluid temperature as described below.

Fitting 20 further includes flow controller or valve 400 extending transversely from an intermediate section of base portion 30 at a position downstream from projection 40 as described above. The flow controller includes housing 410 and valve member 420 with core member 430 as described above. A solenoid or actuator 443 is attached to the proximal end of housing 410 and coupled to controller 125. The solenoid may be integral with the temperature sensing device, or may be releasably secured to housing 410 (e.g., via a threaded, friction fit, or other arrangement, etc.) to enable the solenoid to be reused with other fittings without sterilization and compromising sterility. The solenoid may be implemented by any conventional or other actuator. Connector element or extension member 460 extends axially from a substantially central location on the distal end of solenoid 443 to a substantially central location on the proximal end of core member 430 to enable the solenoid to manipulate the core member.

Controller 125 receives a temperature measurement from temperature sensor 90 as described above. When the measured temperature is within a desired range of the set-point temperature for the fluid, controller 125 (e.g., via temperature controller 170 (FIG. 3)) actuates solenoid 443 to rotate core member 430 within housing 410 to open the flow controller and permit fluid flow. In particular, the core member is rotated (e.g., as indicated by arrow R in FIG. 10D) within the housing by the solenoid to align core member aperture 470 with fluid channel 60 to open the valve and permit fluid flow in substantially the same manner described above. The controller may further actuate the solenoid to further rotate the core member (in the same or opposing direction) to close the flow controller and interrupt the flow. This may occur when the controller determines the fluid temperature measurement to be excessive or beyond a desired range of the set-point temperature. The desired ranges may be entered by a user into controller 125. Temperature sensing device 10 with the controlled flow controller may alternatively be implemented with temperature sensor 90 directly contacting fluid (without receptacle 80) in a manner similar to that described above for FIG. 1.

Operation of temperature sensing device 10 including the controlled twist or ball type flow controller or valve is described with reference to FIG. 10D. Temperature sensing device 10 is attached to IV line 70 by securing base portion open ends 50A, 50B to operator selected portions of the IV line as described above. Flow controller 400 is coupled to controller 125 and typically initially resides in a closed configuration with core member 430 in an orientation preventing aperture 470 of core member 430 from being aligned with channel 60. Upon securing fitting 20 to IV line 70, IV fluid is permitted to flow through the IV line and fitting. Flow controller 400 impedes further flow of the fluid through fitting 20, while temperature sensor 90 measures the temperature of the fluid as described above. The temperature information is transmitted to controller 125 for control and display of the fluid temperature.

When the fluid reaches the desired temperature, controller 125 actuates solenoid 443 to set the flow controller in the opened configuration. Specifically, solenoid 443 rotates (e.g., as indicated by arrow R in FIG. 10D)) core member 430 within housing 410 until the core member aperture 470 and channel 60 are substantially aligned. This enables fluid to flow through longitudinal channel 60 and IV line 70 toward a patient. Controller 125 may further actuate solenoid 443 to rotate the core member (in the same or opposing direction) within housing 410 to close the flow controller when the measured fluid temperature is beyond a desired temperature range. Upon completion of infusion, an IV fluid temperature measurement or medical procedure, temperature sensor 90 and/or solenoid 443 are removed from the fitting for additional use, while the fitting (or IV line set including the fitting) is discarded.

A temperature sensing device for measuring fluid temperature proximate an injection site on a patient is illustrated in FIG. 11. This temperature measurement provides enhanced accuracy since the temperature measurement is performed in close proximity to the fluid entry site on a patient. In other words, the temperature of the fluid is measured just before entering the patient. Specifically, temperature sensing device 510 includes a fitting 520 and a needle hub 555. Fitting 520 includes a substantially cylindrical base portion 530 and a generally cylindrical projection 540 extending transversely from an intermediate section of the base portion. Base portion 530 may include a first open end 550A and a second open end 550B and a fluid conduit or channel 560 defined longitudinally therethrough to permit fluid flow. Projection 540 is substantially similar to projection 40 described above and includes open ends that facilitate access to channel 560.

Fitting 520 is preferably in the form of a one-way valve to prevent back flow from needle hub 555 during infusion. However, the fitting may be implemented by any of the temperature sensing devices described above, or by any suitable conventional or other flow controllers or valves (e.g., one or two way valves, etc.). First open end 550A of base portion 530 may be removably secured to IV line 70, while second open end 550B may be removably secured to needle hub 555. Typically, each base portion open end 550A, 550B may be releasably secured to IV line 70 and/or needle hub 555 via a Luer lock or other suitable connector 75. Fitting 520 may be removed from IV line 70 (or the needle hub) and discarded to maintain fluid sterility. Alternatively, fitting 520 may be permanently secured to IV line 70 and needle hub 555 (e.g., by welding the ends of the fitting to portions of the IV line and needle hub) to form a disposable IV line set. Base portion 530 may further include a plunger or ball type flow controller 300, 400 (FIGS. 9A-10D) as described above that is positioned between projection 540 and needle hub 555 to control fluid flow to a patient as described above.

Needle hub 555 directs fluid from fitting 520 to a needle 565 disposed within the needle hub distal end and inserted into a patient. The needle may be implemented by any conventional or other needle suitable for injection of intravenous fluids. The needle hub includes a shaft 556 defining a conduit or channel 557 therein to permit fluid flow through the shaft. Shaft conduit 557 extends from an open needle hub proximal end to a hub open distal end and is in fluid communication with needle 565 and channel 560 of fitting 520. Shaft 556 is generally conical, but may be of any suitable shape. The needle hub proximal end is secured to fitting 520 via a Luer lock or other suitable connector 75. A pair of wing-shaped control members 558 may extend transversely from an intermediate section of shaft 556 to assist a user in gripping device 510 and inserting the needle into a patient.

A thermally conductive receptacle 80 is secured within projection 540 and extends partially within base portion 530 for contacting fluid flowing within base portion channel 560. Receptacle 80 is substantially similar to the receptacle described above for FIG. 5 and includes generally cylindrical body 82 with closed distal end 84 that extends partially within the base portion 530, and open proximal end 86 for receiving temperature sensor 90 as described below. Flange 88 extends radially from the open proximal end of the receptacle to engage an interior surface of projection 540. Receptacle 80 includes dimensions sufficient to provide a fluid tight seal between projection 540 and base portion channel 560 to maintain the fluid within the channel in substantially the same manner described above. Fitting 520 may be constructed of plastic or any other rigid material suitable for use with IV lines. Fitting 520 typically includes a T-type configuration, however, any configuration (e.g., a Y-type fitting, cross fitting, coupling, etc.) may be utilized. In addition, temperature sensing device 510 may further include any of the securing mechanisms described above (e.g., FIGS. 6-7, threaded engagement, friction fit, etc.) to secure temperature sensor 90 to fitting 520 and properly position the temperature sensor within receptacle 80. Temperature sensing device 510 may alternatively be implemented with temperature sensor 90 directly contacting fluid (without receptacle 80) in a manner similar to that described above for FIG. 1. The temperature sensor is substantially similar to the temperature sensor described above. Sensor wiring 95 may connect temperature sensor 90 to monitor device 100 for display of the measured fluid temperature, or to controller 125 for control (e.g., of thermal treatment devices) and display of the fluid temperature as described above.

Operation of temperature sensing device 510 is described with reference to FIG. 11. Initially, first open end 550A of the base portion is attached to IV line 70, and second open end 550B is secured to the needle hub. Upon securing fitting 520 to both IV line 70 and needle hub 555 in a fluid tight relationship, IV fluid is permitted to flow through the IV line and fitting. The distal end of receptacle 80 contacts fluid flowing through fitting 520. Temperature sensor 90 is inserted into the receptacle with the distal end of the temperature sensor contacting the receptacle closed end.

The fluid transfers heat to receptacle 80 to cause the receptacle to substantially attain the fluid temperature. Temperature sensor 90 directly measures the temperature of the receptacle, thereby indirectly measuring the temperature of the fluid. The temperature sensor transmits the measured temperature information via sensor wiring 95 to monitor device 100 for display of fluid temperature, or to controller 125 for display and control of the fluid temperature as described above. The controller processor (FIG. 3) may produce reports from information received from the temperature controller and/or the processor input devices as described above. Upon completion of infusion, an IV fluid temperature measurement or medical procedure, temperature sensor 90 is removed from fitting 520 for additional use, while the fitting (or the IV line set including the fitting) is discarded.

Figure 12:
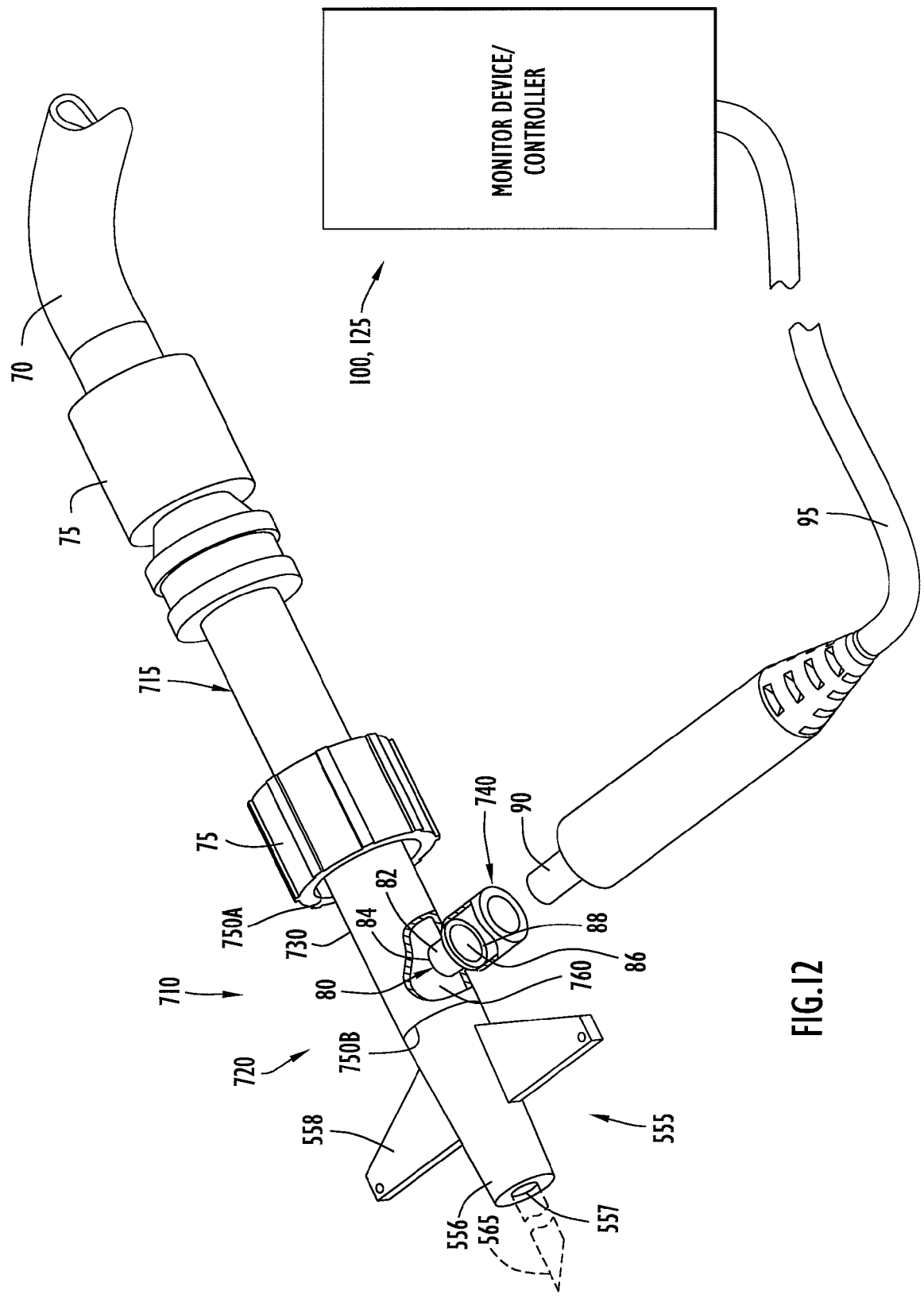
FIG. 12 is a view in perspective of an alternative embodiment of the temperature sensing device of FIG. 11 measuring temperature of fluid proximate a patient entry site according to the present invention.

A temperature sensing device that enables temperature measurement of fluid within a needle hub is illustrated in FIG. 12. Specifically, temperature sensing device 710 includes a fitting 720 and needle hub 555. Fitting 720 includes a substantially cylindrical base portion 730 with an open ends 750A, 750B and a channel 760 defined longitudinally therethrough to permit fluid flow. Open end 750A of base portion 730 may be removably secured to a valve 715 via a Luer lock or other suitable connector 75. The valve is preferably implemented by a conventional one-way valve to prevent back flow from the needle hub during infusion. However, the valve may be implemented by any suitable flow control mechanism (e.g., one or two way valve, etc.). The valve is further coupled to IV line 70 via Luer lock or other suitable connector 75.

Fitting 720 further includes a generally cylindrical projection 740 extending transversely from an intermediate section of the base portion. Projection 740 is substantially similar to projection 40 described above and includes open ends that facilitate access to fluid channel 760 within the base portion. A thermally conductive receptacle 80 is secured within projection 740 and extends partially within base portion 730 for contacting fluid flowing within base portion channel 760. Receptacle 80 is substantially similar to the receptacle described above for FIG. 5 and includes generally cylindrical body 82 with a closed distal end 84 that extends partially within base portion 730, and open proximal end 86 for receiving temperature sensor 90 as described below. Flange 88 extends radially from the open proximal end of the receptacle to engage an interior surface of projection 740. Receptacle 80 includes dimensions sufficient to provide a fluid tight seal between projection 740 and base portion channel 760 to maintain the fluid within the channel in substantially the same manner described above. Fitting 720 may be constructed of plastic or any other rigid material suitable for use with IV lines. Fitting 720 typically includes a T-type configuration, however, any configuration (e.g., a Y-type fitting, cross fitting, coupling, etc.) may be utilized. The temperature sensor is substantially similar to the temperature sensor described above. Sensor wiring 95 may connect temperature sensor 90 to monitor device 100 for display of the measured fluid temperature, or to controller 125 for control (e.g., of the thermal treatment devices) and display of the fluid temperature as described above.

Base portion 730 may further include a plunger or ball type flow controller 300, 400 (FIGS. 9A-10D) as described above that is positioned between projection 740 and needle hub 555 to control fluid flow to a patient as described above. In addition, temperature sensing device 710 may further include any of the securing mechanisms described above (e.g., FIGS. 6-7, threaded engagement, friction fit, etc.) to secure temperature sensor 90 to fitting 520 and properly position the temperature sensor within receptacle 80. Temperature sensing device 710 may alternatively be implemented with temperature sensor 90 directly contacting fluid (without receptacle 80) in a manner similar to that described above for FIG. 1.

Needle hub 555 is substantially similar to the needle hub described above and is directly secured to distal end 750B of base portion 730. Fitting 720 may be removed from the needle hub and valve and discarded to maintain fluid sterility. Alternatively, fitting 720, needle hub 555, valve 715 and/or IV line 70 may be permanently secured to each other (e.g., by welding, etc.) in any suitable combinations to form a disposable IV line set. Needle hub 555 directs fluid from valve 715 to needle 565 disposed within the needle hub distal end and inserted into a patient. The needle may be implemented by any conventional or other needle suitable for injection of intravenous fluids. The needle hub includes shaft 556 defining conduit or channel 557 therein to permit fluid flow through the shaft. Shaft conduit 557 extends from an open needle hub proximal end to a hub open distal end and is in fluid communication with needle 565 and channel 760 of fitting 720. The needle hub proximal end is directly secured to fitting 720 (e.g., friction fit, etc.). Wing-shaped control members 558 may extend transversely from an intermediate section of shaft 556 to assist a user in gripping device 710 and inserting the needle into a patient.

Operation of temperature sensing device 710 is described with reference to FIG. 12. Open end 750A of base portion 730 is attached to IV line 70 and second open end 750B is secured to needle hub 555. Upon securing fitting 720 in a fluid tight relationship, IV fluid is permitted to flow through the IV line, fitting and needle hub toward a patient. The distal end of receptacle 80 contacts fluid flowing through fitting 720. Temperature sensor 90 is inserted into the receptacle with the distal end of the temperature sensor contacting the receptacle closed end.

The fluid transfers heat to receptacle 80 to cause the receptacle to substantially attain the fluid temperature. Temperature sensor 90 directly measures the temperature of the receptacle, thereby indirectly measuring the temperature of the fluid. The temperature sensor transmits the measured temperature information via sensor wiring 95 to monitor device 100 for display of fluid temperature, or to controller 125 for display and control of the fluid temperature as described above. The controller processor (FIG. 3) may produce reports from information received from the temperature controller and/or the processor input devices as described above. Upon completion of infusion, an IV fluid temperature measurement or medical procedure, temperature sensor 90 is removed from fitting 720 for additional use, while the fitting (or the IV line set including the fitting) is discarded.

It will be appreciated that the embodiments described above and illustrated in the drawings represent only a few of the many ways of implementing a method and apparatus for measurement and control of temperature for infused liquids.

The temperature sensors or probes of the temperature sensing devices described above may be implemented by any quantity of any type of conventional or other temperature measuring devices (e.g., RTD, IR, NTC, thermistors, thermocouples, etc.). The sensors may be of any shape or size to accommodate a particular application. The monitor device and controller described above may be implemented by any quantity of any conventional or other processing devices or circuitry to determine, display and/or control fluid temperature. The monitor device and controller may include various indicators (e.g., visual, audio, speech synthesis, etc.) to indicate the measured temperature and notify of occurrence of any type of temperature or other conditions. The temperature sensors and flow controllers may communicate with the monitor device and/or controller via any communications medium (e.g., wired, wireless, IR, etc.).

The monitor device and controller may include any quantity of any type of conventional or other displays (e.g., LCD, LED, etc.) of any size or shape disposed at any suitable locations. The monitor device and controller may display any desired information (e.g., time, temperature, date, patient information, etc.), and may be disposed at any locations (e.g., near or away from the temperature sensing device) within view of an operator. The monitor device and controller may employ any type of input devices (e.g., keypad, buttons, voice recognition, touch screen, etc.) and may further include any types of processing, printing and/or recording devices to process, print and/or record any desired information in any desired fashion.

The temperature sensing device fittings described above may be of any quantity, shape, or size, may be constructed of any suitable materials, and may be disposed at any suitable locations along an IV or other medical line. The fitting base and projection may be of any quantity, shape, or size and may be constructed of any suitable materials. The base channel may be of any shape or size, may be defined in the base at any locations and extend in any desired directions. The channel preferably includes uniform dimensions; however, the channel may include uniform or fluctuating dimensions (e.g., uniform, progressively increasing/decreasing dimensions, steps or shoulders, etc.). The fluid line may be secured to the fitting via any conventional or other locks or connectors. The base and projection may be arranged or connected in any fashion, while the fitting may have any suitable configuration (e.g., T-type fitting, Y-type fitting, cross fitting, coupling, etc.). The fitting may be included within and permanently or releasably connected to a disposable IV line set. The temperature sensor may be disposed within the fitting projection in any manner via any conventional or other securing mechanisms (e.g., friction fit, adhesives, clamp, threaded engagement, etc.). The fitting may include a receptacle to maintain fluid sterility and permit re-use of the temperature sensor.

The conductive receptacle may be of any quantity, shape, or size, may be constructed of any suitably thermally conductive materials, and may be disposed at any locations within the projection or fitting suitable to contact or thermally conduct heat from fluid flowing within the fitting. The conductive receptacle body and flange may be of any quantity, shape, or size and may be constructed of any suitable materials. The temperature sensor may be secured within the receptacle via any conventional or other securing techniques (e.g., friction fit, threaded engagement, securing mechanism, etc.). Similarly, the receptacle may be secured within the projection or fitting via any conventional or other securing techniques (e.g., friction fit, adhesives, threaded engagement, securing mechanism, etc.).

The control circuit components (e.g., power supply, power switch, thermostat, temperature controller, microprocessor, communications module, etc.) may be implemented by any conventional or other components arranged in any suitable fashion and performing the functions described herein. The power supply may be implemented by any quantity of any conventional or other power supply devices and may receive AC and/or DC power signals and provide AC and/or DC power signals at any appropriate power levels to the control circuit components. The power switch may be implemented by any quantity of any conventional or other suitable switching devices (e.g., button, switch, etc.). The thermostat may be of any quantity and may be implemented by any conventional or other switching type or limiting devices (e.g., a high limit thermostat, etc.). The indicators may be implemented by any quantity of any conventional or other visual and/or audio indicators (e.g., beeper or buzzer, speaker, various colored light emitting diodes (e.g., green diode, yellow diode and red diode), etc.) to inform an operator of the measured temperature.

The temperature controller may be implemented by any quantity of any conventional or other temperature controller or processor (e.g., chip, card, processor, circuitry, etc.) and include any quantity of any desired input devices (e.g., buttons, keypad, etc.). The temperature controller may control the thermal treatment devices to any desired temperature range, and may utilize any quantity of set points (e.g., maximum and/or minimum, etc.). The system may record any type of information (e.g., date and time of thermal treatment disablement and enablement, fluid level or loss, etc.) relating to system operation for subsequent retrieval, analysis, display, display/report and control functions.

The control circuit processor may be implemented by any quantity of any conventional or other processing device (e.g., microprocessor, controller, circuitry, logic, etc.). The report may be arranged in any fashion and include any desired information (e.g., start date and start time of solution thermal treatment, the time interval the solution was thermally treated, the temperature the solution attained during thermal treatment (e.g., partial or complete history of time and solution temperature), facility name and location, patient information, doctor information, type of procedure, type of solution being thermally treated, amount of solution being thermally treated, etc.). The processor or system display may be implemented by any conventional or other display of any shape or size and may be disposed on the controller at any desired location. The display may display any desired information (e.g., the elapsed (or running) time, report, etc.). The information displayed may be selected via processor input devices or display controls (e.g., buttons, keys, etc.).

Software for the temperature controller and processor may be implemented in any desired computer language and could be developed by one of ordinary skill in the computer arts based on the functional descriptions contained herein. The temperature controller and/or processor may alternatively be implemented by any type of hardware and/or other processing circuitry, and may be available pre-programmed for immediate use. The various functions of the temperature controller and/or processor may be distributed in any manner among any quantity of software modules, processors and/or circuitry.

The printer may be implemented by any quantity of any conventional or other printing device. The processor may control the printer to produce the report at specified times (e.g., termination of treatment, at particular times of day, after a particular quantity of uses, etc.) or in response to requests from medical personnel via processor input devices (e.g., print key). The communications module may be implemented by any quantity of any conventional or other communication device (e.g., router, modem, NIC, etc.) and enables communication with other devices for transference or downloading of information. Moreover, the communications module may facilitate retrieval of information (e.g., patient information, facility information, doctor information, solution information, instrument information, etc.) from a database or other source.

The securing cap may be of any quantity, shape, or size and may be constructed of any suitable materials. The cap channel may be of any shape or size, may be defined at any cap locations and may extend in any desired directions. The temperature probe may be secured within the securing cap via any conventional or other securing techniques (e.g., friction fit, threaded engagement, securing mechanism, etc.). The projection tabs may be of any quantity, shape or size, may be constructed of any desired materials and may be disposed at any locations on the projection or fitting. The channel grooves and notches may be of any quantity, shape, or size and may be defined at any locations. The tabs may be secured to the projection or fitting in any manner enabling fracture or removal of the tabs. The securing mechanism may be implemented with any of the temperature sensing device embodiments described above employing a reusable temperature sensor (e.g., employing the receptacle to receive the temperature sensor).

The looped configuration may include any quantity of loops or windings within the fluid flow path, where the loops or windings may surround any quantity of temperature sensors and/or receptacles. The housing portion may be of any size or shape, and may be constructed of any suitable materials. The temperature sensor and/or receptacle may be partially or fully disposed within the housing portion. Alternatively, the looped configuration may be employed without the housing portion, where the loop surrounds the temperature sensor and/or receptacle. The looped path may be defined by any conventional or other techniques. For example, the base portion may be preconfigured in a looped arrangement, or include a tubular member configured in a looped arrangement. Further, the housing portion may contain any quantity of dividers or guides to direct the fluid flow in a looped path through the housing. Further, the housing portion may simply contain the fluid to surround the temperature sensor and/or receptacle.

The flow controllers may be of any quantity, shape, or size, may be constructed of any suitable materials, and may be disposed at any suitable locations along the fittings or line. The flow controllers may be implemented by any quantity of any conventional or other flow control devices (e.g., valves, etc.) with any type of actuating mechanism (e.g., piston, rotation, etc.). Any quantity of flow controllers may employed on a temperature sensing device. The core members and gripping members may be of any quantity, shape, or size and may be constructed of any suitable materials. The housings may be of any quantity, shape, or size and may be constructed of any suitable materials. The apertures defined within the core members and/or housings may be of any size and shape and disposed at any suitable location to control fluid flow. The apertures may be defined to have any desired alignment/misalignment with the fitting fluid channel to control fluid flow. The connection members may be of any shape or size and may be constructed of any suitable materials.

The piston type flow controller may include any suitable locking mechanism (e.g., projection and recess or notch, clamping or interlocking arrangement, etc.) employing any mated or engaging components. The rib and corresponding recess may be of any quantity, size or shape and may be disposed at any suitable locations. These components may be disposed on the core member or housing in any fashion. For example, the rib may be disposed on the housing while the core member includes a corresponding recess. The gripping member of the piston type flow controller may be urged distally into the housing for any desired amount to control the fluid flow (e.g., full flow, partial flow or no flow).

The rotational type flow controller may include any suitable locking mechanism (e.g., projection and recess or notch, clamping or interlocking arrangement, etc.) employing any mated or engaging components. The shoulders and grooves may be of any quantity, size or shape and may be disposed at any suitable locations. These components may be disposed on the gripping member or housing in any fashion. The gripping member of the rotational flow controller may be rotated at any desired amount to control the fluid flow (e.g., full flow, partial flow or no flow). The core member of the rotational flow controller may include a distal portion of any shape or size (e.g., spherical, cylindrical, uniform with the core member proximal portion, etc.). The securing plate may be of any quantity, shape or size, may be constructed of any suitable materials and may be disposed at any locations to secure the core member.

The solenoids may be implemented by any quantity of any conventional or other actuators, and may apply forces in any suitable direction or orientation to operate the valves (e.g., linear, rotational, etc.). The controller may actuate the valves to open or close in response to any suitable comparison (e.g., within or beyond the desired temperature or temperature range) of the measured temperature with the desired temperature or temperature range. The flow controllers may be implemented with any of the temperature sensing device embodiments described above.

The needle hub may be of any quantity, shape, or size, and may be constructed of any suitable materials. The shaft and control members may be of any quantity, shape, or size and may be constructed of any suitable materials. The control members may be disposed at any suitable locations. The shaft conduit may be of any shape or size. The needle hub may receive any quantity or size of any types of conventional or other needles. The valve may be implemented by any suitable valve (e.g., one way, two way, etc.). The projection may be disposed at any suitable location prior to, on or between the valve and needle hub. The needle hub, valve and fitting may be formed as an integral unit, or may be coupled together, in any suitable combinations or arrangements.

It is to be understood that the present invention is not limited to the specific configurations or applications described above, and may be utilized to determine the temperature of a fluid at any desired location within any type of medical or other fluid line. The temperature sensing device may be secured to the fluid line via any suitable fastening techniques (e.g., connectors, etc.).

The temperature sensing devices described above may be employed with any types of infusion apparatus, such as the apparatus shown in FIG. 2. The temperature sensing devices described above may be placed at any desired locations along a fluid line (e.g., attached to those locations) via any suitable attachment or placement techniques to measure temperature of fluid at those locations. The manners of operation of the temperature sensing devices described above may be modified in any fashion to perform fluid temperature measurement and/or control. A fluid line may include any quantity of temperature sensing devices, where temperature measurements may be combined in any fashion (e.g., averaged, weighted, etc.) to determine a fluid temperature.

The temperature sensing devices may be employed for any types of fluid lines (e.g., medical or other lines, etc.) and corresponding fluids (e.g., intravenous or irrigation fluids, solutions or gases, non-medical fluids, etc.) for temperature measurement and/or control. In addition, the thermal treatment devices may be implemented by any conventional or other type of heating and/or cooling elements (e.g., pads, wires, devices employing heat exchange fluids, heating coils, cooling coils, etc.), and may thermally treat fluid to any suitable desired temperature or temperature range. These devices may be disposed at any suitable locations (e.g., proximate a solution bag or fluid source, along a fluid line, etc.), and may thermally treat (e.g., heat and/or cool) fluid to any desired temperature range.

It is to be understood that the terms "top", "bottom", "front", "rear", "side", "height", "length", "width", "upper", "lower", "downward", "upward" and the like are used herein merely to describe points of reference and do not limit the present invention to any particular orientation or configuration.

From the foregoing description, it will be appreciated that the invention makes available a novel method and apparatus for measurement and control of temperature for infused liquids, wherein temperature sensing devices monitor temperature of an intravenous fluid at any desirable location along a fluid line, and may further selectively enable and/or disable the flow of fluid to ensure a desired fluid temperature is attained within the fluid line prior to entering a patient.

Having described preferred embodiments of a new and improved method and apparatus for measurement and control of temperature for infused liquids, it is believed that other modifications, variations, and changes will be suggested to those skilled in the art in view of the teachings set forth herein. It is therefore to be understood that all such variations, modifications, and changes are believed to fall within the scope of the present invention as defined by the appended claims.

What is claimed is:

1. A temperature sensing device for measuring temperature of a sterile medical fluid comprising:
   a medical fluid container to house a sterile medical fluid;
   a fluid line coupled to said medical fluid container to receive said sterile medical fluid therefrom and direct said medical fluid toward a patient;
   a thermal treatment device proximate said fluid line and operable to thermally treat said sterile medical fluid proximate said thermal treatment device;
   a conduit member disposed at a selected location along said fluid line and including;
      a first open end and a second open end, each end being directly securable to selected portions of said fluid line; and
      an elongated non-linear tubular body extending between said first and second open ends and forming a non-linear flow path for said sterile medical fluid flowing within said fluid line, wherein said non-linear tubular body includes at least one curved section and a thermally conductive flow member directing flow of and in contact with said sterile medical fluid within said at least one curved section;
   a temperature sensor disposed proximate said thermally conductive flow member to measure temperature through said thermally conductive flow member of said sterile medical fluid within said at least one curved section and to generate an electrical temperature signal indicating said measured fluid temperature; and
   a controller coupled to said temperature sensor and said thermal treatment device to control said thermal treatment device to thermally treat said medical fluid to attain a desired temperature based on said measured fluid temperature.

2. The temperature sensing device of claim 1, wherein said desired temperature is entered by a user.

3. The temperature sensing device of claim 1, wherein said thermal treatment device thermally treats said medical fluid in the form of at least one of heating and cooling.

4. The temperature sensing device of claim 1, wherein said controller displays said measured fluid temperature.

5. The temperature sensing device of claim 1, wherein said non-linear tubular body includes a looped configuration.

6. The temperature sensing device of claim 1, further including a needle hub assembly coupled to said conduit member, wherein said needle hub assembly includes a needle to direct said medical fluid from said conduit member into said patient.

7. The temperature sensing device of claim 1, wherein said controller records said measured fluid temperature to generate a report.

8. The temperature sensing device of claim 7, further including a printer to print at least one of said measured fluid temperature and said report.

9. The temperature sensing device of claim 7, wherein said controller includes a communication module to transmit said report to another device.

10. The temperature sensing device of claim 1, wherein said conduit member further includes a flow controller to selectively control flow of said medical fluid through said conduit member.

11. The temperature sensing device of claim 10, wherein said flow controller includes a locking mechanism to maintain said flow controller in a state enabling flow of said medical fluid through said conduit member.

12. The temperature sensing device of claim 10, wherein said flow controller includes a housing and a piston slidably disposed therein, wherein said piston includes an aperture and is selectively manipulated linearly to align said aperture with said flow path to control flow of said medical fluid within said conduit member.

13. The temperature sensing device of claim 10, wherein said flow controller includes a housing and a valve member rotatably disposed therein, wherein said valve member includes an aperture and is selectively rotated to align said aperture with said flow path to control flow of said medical fluid within said conduit member.

14. The temperature sensing device of claim 10, wherein said controller is coupled to said flow controller and manipulates said flow controller to control flow of said medical fluid based on said measured fluid temperature.

15. A method of measuring temperature of a sterile medical fluid flowing within a medical fluid line comprising:
(a) receiving first and second open ends of a conduit member at selected portions of said fluid line, wherein a thermal treatment device is disposed proximate said fluid line and operable to thermally treat said sterile medical fluid proximate said thermal treatment device, and wherein said conduit member further includes an elongated non-linear tubular body extending between said first and second open ends and forming a non-linear flow path for said sterile medical fluid flowing within said fluid line, wherein said non-linear tubular body includes at least one curved section and a thermally conductive flow member directing flow of and in contact with said sterile medical fluid within said at least one curved section;
(b) measuring a temperature through said thermally conductive flow member of fluid within said at least one curved section via a temperature sensor disposed proximate said thermally conductive flow member and generating a temperature signal indicating said measured fluid temperature; and
(c) controlling, via a controller, said thermal treatment device disposed proximate said fluid line to thermally treat said medical fluid to attain a desired temperature based on said measured fluid temperature.

16. The method of claim 15, wherein step (c) further includes:
(c.1) facilitating entry of said desired temperature into said controller by a user.

17. The method of claim 15, wherein said thermal treatment device thermally treats said medical fluid in the form of at least one of heating and cooling.

18. The method of claim 15, wherein step (b) further includes:
(b.1) displaying said measured fluid temperature.

19. The method of claim 15, wherein said non-linear tubular body includes a looped configuration, and step (b) further includes:
(b.1) directing said medical fluid in a looped flow path formed by said looped tubular body.

20. The method of claim 15, wherein said conduit member includes a needle hub assembly coupled to said conduit member, wherein said needle hub assembly includes a needle to direct said medical fluid from said conduit member into a patient, and step (c) further includes:
(c.1) directing said medical fluid into said patient.

21. The method of claim 15, wherein said conduit member further includes a flow controller, and step (b) further includes:
(b.1) selectively controlling flow of said medical fluid through said conduit member.

22. The method of claim 21, wherein step (c) further includes:
(c.1) controlling said flow controller based on said measured fluid temperature.

23. The method of claim 15, further including:
(d) recording, via said controller, said measured fluid temperature to generate a report.

24. The method of claim 23, further including:
(e) printing at least one of said measured fluid temperature and said report via a printer.

25. The method of claim 23, further including:
(e) transmitting said report to another device via a communication module.

* * * * *